United States Patent
Levitan et al.

(10) Patent No.: US 8,815,071 B2
(45) Date of Patent: Aug. 26, 2014

(54) MANIPULATION, DETECTION, AND ASSAY OF SMALL SCALE BIOLOGICAL PARTICLES

(75) Inventors: Steven P. Levitan, Pittsburgh, PA (US); Samuel J. Dickerson, Pittsburgh, PA (US); Donald M. Chiarulli, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 0 days.

(21) Appl. No.: 13/596,707

(22) Filed: Aug. 28, 2012

(65) Prior Publication Data

US 2013/0222802 A1   Aug. 29, 2013

Related U.S. Application Data

(62) Division of application No. 12/175,340, filed on Jul. 17, 2008, now Pat. No. 8,278,188.

(51) Int. Cl.
| | |
|---|---|
| *H01L 21/30* | (2006.01) |
| *B03C 5/00* | (2006.01) |
| *B03C 5/02* | (2006.01) |
| *G01N 27/447* | (2006.01) |
| *G01N 15/02* | (2006.01) |
| *G01N 15/00* | (2006.01) |
| *B01L 3/00* | (2006.01) |

(52) U.S. Cl.
CPC ....... *G01N 27/447* (2013.01); *B01L 2300/0819* (2013.01); *B03C 5/005* (2013.01); *B03C 5/026* (2013.01); *G01N 15/0266* (2013.01); *G01N 2015/0038* (2013.01); *G01N 2015/0288* (2013.01); *B01L 2300/0645* (2013.01); *B01L 2400/0415* (2013.01); *B01L 2300/0636* (2013.01); *B01L 3/502715* (2013.01); *G01N 15/0205* (2013.01); *B01L 2200/0647* (2013.01); *B01L 3/502761* (2013.01); *B03C 2201/26* (2013.01)
USPC ........................................ 204/643; 359/207.7

(58) Field of Classification Search
CPC .................. B01L 2400/0415; B01L 3/502715; B01L 3/502761; B01L 3/502769; B03C 5/005; B03C 5/026; B03C 2201/18; B03C 2201/22; G01N 15/0205; G01N 15/0266; G01N 2015/0288; G01N 27/447
USPC ............ 204/643; 359/24.5, 207.7, 211.6, 563
See application file for complete search history.

(56) References Cited

PUBLICATIONS

Machine translation of JP 2006-058196, A.*
Dickerson, S.J. et al. "Three-dimensional integrated circuits for lab-on-chip dielectrophoresis of nanometer scale particles", Microfluidics, BioMEMS, and Medical Micrsystems, V; Proceedings of SPIE, vol. 6465, Jan. 20-25, 2007, p. 64650J1-9.

* cited by examiner

*Primary Examiner* — J. Christopher Ball
(74) *Attorney, Agent, or Firm* — Kegler Brown Hill & Ritter; James J. Pingor

(57) ABSTRACT

Systems, devices, and methods are presented that facilitate electronic manipulation and detection of submicron particles. A particle manipulation device contains a plurality of electrodes formed on an active semiconductor layer of an integrated circuit chip, where the electrodes and gap spacing between adjacent electrodes is submicron in size. The chip is oriented with its substrate face up, and at least a portion of the substrate is removed from the chip so the electrodes are in close proximity to a fluid chamber(s) placed over the chip, to facilitate manipulation of particles, contained in a buffer solution in the fluid chamber(s), to form a defined pattern. Innovative macro-scale optical detection is employed to detect the submicron particles, where a light beam is applied to the defined pattern, and interaction of the defined pattern with the light beam is detected and evaluated to facilitate detecting the particles.

16 Claims, 17 Drawing Sheets

MANIPULATION, DETECTION, AND ASSAY OF SMALL SCALE BIOLOGICAL PARTICLES

CROSS-REFERENCE TO RELATED APPLICATION

This application is Divisional of pending U.S. patent application Ser. No. 12/175,340 entitled "MANIPULATION, DETECTION, AND ASSAY OF SMALL SCALE BIOLOGICAL PARTICLES" and filed Jul. 17, 2008 which claims the benefit of U.S. Provisional Patent application Ser. No. 60/950,756 entitled "Three-dimensional integrated circuits for lab-on-chip dielectrophoresis of nanometer scale particles" and filed Jul. 19, 2007. The entireties of the above-referenced applications are incorporated by reference herein.

TECHNICAL FIELD

The subject innovation generally relates to electronic manipulation and detection of small scale particles and in particular to systems, devices, and methods that can facilitate efficient dielectrophoresis and detection of small scale particles. Small scale particles in this context refers generally to objects with dimensions equal to or smaller than 1-100 um, (e.g., biological cells) and particularly to objects with dimensions of nanometer scale and below (e.g., viruses, components of viruses, and biological macromolecules).

BACKGROUND

Labs-on-chips, which can be similar to systems-on-a-chip, can be used to attempt to offer desired economical solutions for biomedical applications. For instance, labs-on-chips can combine, in monolithic form, sample containment, transportation (e.g., microfluidic), programmability, and detection for bio-sensing. Lab-on-chip miniaturization can facilitate devices that operate with low power, are capable of low cost, portable implementations, have reduced sample size requirements, and better resolution for bio-sensing.

Dielectrophoresis can be used in a broad range of lab-on-chip applications such as cytometry, cell sorting, and mixture separation. Conventionally, due to technology limitations, many implementations are limited to fabricating dielectrophoresis electrodes that are on a scale of 10 s of microns or larger, and therefore, it is desirable to implement a system with large numbers of small and dense electrodes that can manipulate small micron and nanometer scale particles (e.g., viruses), using densely integrated systems.

Also, when dealing with nanometer scale particles, such that the size of the particles is smaller than the diffraction limit of visible light, it can be difficult to optically detect such particles, as the particles are so small that the use of optical microscopy to directly view the particles is not possible. Therefore, it is desirable to develop a method to manipulate small scale particles into ordered arrangements that can be detected and assayed using macro-scale optical systems.

SUMMARY

The following presents a simplified summary in order to provide a basic understanding of some aspects of the disclosed subject matter. This summary is not an extensive overview of the disclosed subject matter and is not intended to identify key/critical elements or to delineate the scope of such subject matter. Its sole purpose is to present some concepts in a simplified form as a prelude to the more detailed description that is presented later.

Systems, devices, and/or methods are presented that can implement large and dense arrays of electrodes that facilitate efficient electronic manipulation (e.g., employing electrophoresis (EP), dielectrophoresis (DEP) or multiple frequency dielectrophoresis (MFDEP)) and detection of small scale particles. In accordance with an embodiment, an integrated circuit wafer can be oriented so that the top surface of the wafer (e.g., the metal interconnection layers) can be face down and bonded to a support structure (e.g., circuit board, packaging device, ceramic interposer, or another silicon wafer in a vertical chip stack) so that the handle silicon (e.g., substrate) on the integrated circuit wafer is oriented face up vertically. The handle silicon can be removed either completely (e.g., grinded off) from the integrated circuit wafer or removed in part (e.g. by chemically etching a pattern) so that the active semiconductor (e.g., doped silicon or polysilicon) layers can be exposed to or at least can be close to the face-up surface of the integrated circuit wafer. A plurality of electrodes can be formed in an active semiconductor layer(s) which can support the formation of features (e.g., electrode size and electrode-to-electrode separation) at the smallest, or at least a significantly smaller, available dimension of an integrated circuit fabrication process (e.g., nanometer scale in size). One or more micro-fluidic structures (e.g., fluidic channels, fluidic chambers, and/or fluidic reservoirs) can be formed in a region(s) over the plurality of electrodes. As a result, the plurality of electrodes can be in close proximity to one or more of the micro-fluidic structure(s). The proximity of the microfluidic chamber(s) and the density of the electrode array(s) can facilitate operating the electrodes with significantly lower applied voltage and significantly greater spatial granularity in a non-uniform field pattern (e.g., dielectrophoresis field).

In accordance with an aspect, a buffer solution comprising particles (e.g., one or more disparate types of submicron particles) can be placed in the micro-fluidic chamber(s). In another aspect, an electrokinetic technique (e.g., EP, DEP, and/or MFDEP) can be employed to facilitate arranging particles into a defined spatial pattern. One or more voltage waveforms having respective frequencies can be applied to a subset(s) of electrodes to facilitate generating a spatially non-uniform electric field(s) that can be applied to the particles to facilitate manipulating, for various separation and isolation operations based at least in part on one or more physical properties of the particles (e.g., size, mass, or electrical conductivity), the particles into desired special regions of a micro-fluidic chamber or for the formation of specific spatial patterns of particles in the micro-fluidic chamber (e.g., parallel lines corresponding to a diffraction grating).

In accordance with another embodiment, multiple frequencies of voltage waveforms can be applied to respective subsets of electrodes (e.g., MFDEP) to facilitate differential manipulation of one or more disparate types of particles in a mixture of particles contained in a buffer solution in a fluidic chamber(s). For example, the particles can be manipulated and trapped such that a specific region of the chamber or subset of a spatial pattern within the chamber (e.g., one or more diffraction grating lines) populated with a first type of particle can be formed based at least in part on a first frequency, and one or more other subsets of spatial patterns within the chamber (e.g., one or more diffraction grating lines) respectively containing a disparate type(s) of particles can be formed in the fluidic chamber based at least in part on a disparate frequency(ies), to facilitate detection of the respective types of particles.

In accordance with still another embodiment, a particle detector component can employ innovative macro-scale optical detection techniques to facilitate detecting small scale particles (e.g., nanometer scale particles, such as certain viruses or other biomaterial) contained in the fluidic chamber(s). In an aspect, a light beam can be applied to particles trapped in the form of a defined spatial pattern, and the defined spatial pattern can interact with the incident light beam such that the interaction between the incident light beam and defined spatial pattern can be detectable by the particle detector component, which can facilitate detection of the trapped particles by the particle detector component.

For instance, when particles are manipulated and trapped, as desired, into a spatial pattern, such as a diffraction grating, the particle detector component can transmit a light beam having a specified wavelength onto the diffraction grating, or a portion thereof, to facilitate obtaining an optical readout of optical power at an angle corresponding to one of the diffraction orders for the diffraction grating, or portion thereof. The angle is determined by the wavelength of the input light beam, the distance between adjacent diffraction grating lines (e.g., spatial period), and the diffraction order selected. The optical power at the detection angle depends on the optical power at the readout wavelength of the incident light, the order selected and the efficiency (e.g., quality) of the diffraction grating. The efficiency of the grating is in turn related to the density of particles trapped into the lines of the grating pattern. Information relating to detection and assay of respective particles in the buffer solution can be provided to a user by measuring the optical power of the diffracted light at the corresponding diffraction angle when diffracted from a region of the spatial grating pattern populated with particles of a specific type. This information can be calibrated against known assays to obtain accurate measurements of particle populations. To facilitate the operation of the grating in reflective rather than transmissive mode, in one embodiment, the bottom surface of the fluidic chamber(s) can be formed of, or can have placed thereon, a reflective material.

In accordance with an aspect, a lab-on-chip(s) that can manipulate small scale particles can be fabricated with analog and digital control electronics incorporated into the lab-on-chip device. In an embodiment, the analog and digital control electronics can be implemented on the same integrated circuit chip as the electrode array. In another embodiment, the analog and digital control electronics can be implemented in a "3D integrated circuit" in which a plurality of integrated circuit chips are positioned in a vertically tiered manner. Each of the integrated circuit chips are comprised of metal layers for interconnect and semiconductor layers for electronic devices. The vertical stack is arranged such that at least the top chip is mounted with the metal interconnect layers on the bottom and the active semiconductor layers on the top. For example, there can be a lab-on-chip comprising three integrated circuit chips, where the top chip can be comprised of the plurality of electrodes and the bottom two chips can comprise a plurality of selector components and a plurality of control components, respectively, that can facilitate generation, control, or selection of the voltage waveforms routed to each electrode.

In accordance with various embodiments, methods that can facilitate electronically manipulating small particles by applying multiple frequencies in spatial and/or temporal sequences to facilitate manipulating particles, and optically detecting particles are disclosed. Further, in accordance with various embodiments, systems and methods that can facilitate manipulating and detecting of particles are disclosed.

To the accomplishment of the foregoing and related ends, certain illustrative aspects are described herein in connection with the following description and the annexed drawings. These aspects are indicative of various ways in which the disclosed subject matter may be practiced, all of which are intended to be within the scope of the disclosed subject matter. Other advantages and novel features may become apparent from the following detailed description when considered in conjunction with the drawings.

DETAILED DESCRIPTION

Figure 1:
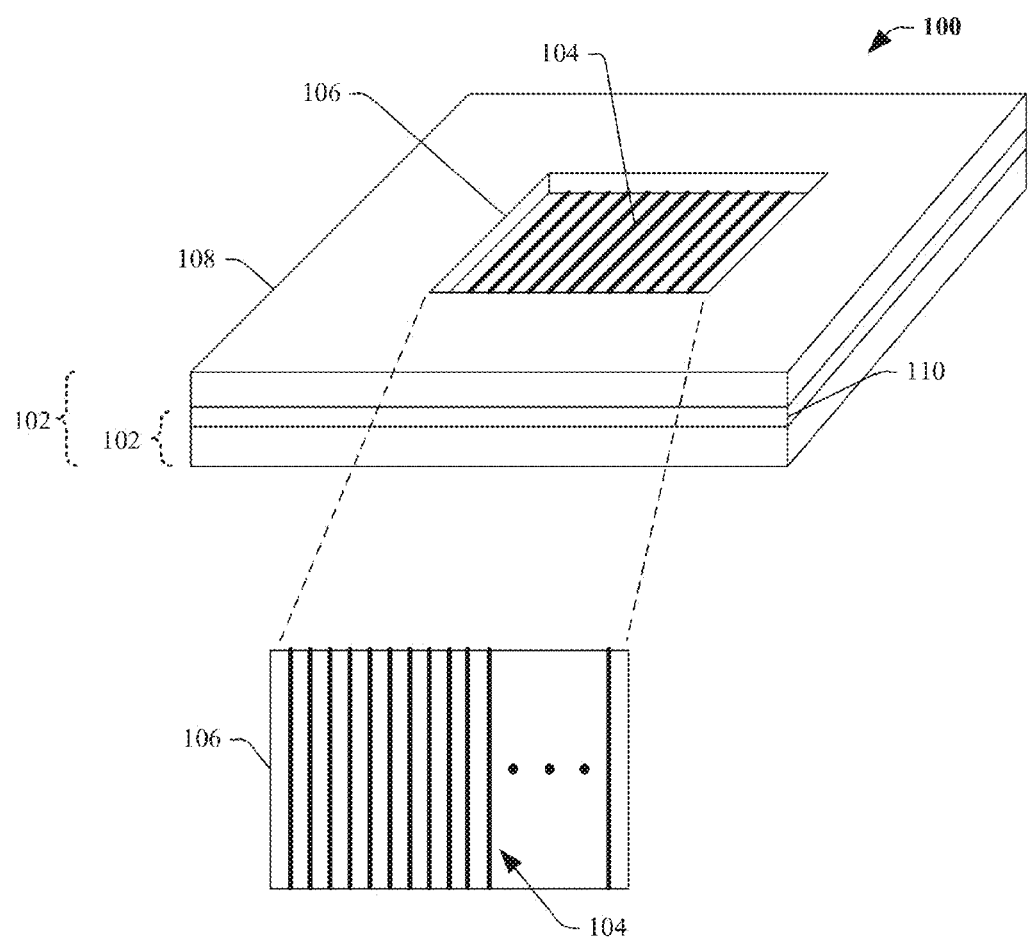
FIG. 1 illustrates a diagram of a device that can facilitate electronic manipulation and detection of small scale particles in accordance with an aspect of the disclosed subject matter.

The various aspects of the disclosed subject matter are now described with reference to the annexed drawings, wherein like numerals refer to like or corresponding elements throughout. It should be understood, however, that the drawings and detailed description relating thereto are not intended to limit the disclosed subject matter to the particular form disclosed. Rather, the intention is to cover all modifications, equivalents, and alternatives falling within the spirit and scope of the disclosed subject matter.

Conventionally, dielectrophoresis (DEP) of particles has been performed on particles on a micron scale or larger due to limitations associated with conventional integrated circuit devices and processes. For instance, conventional systems and devices have been restricted to fabricating DEP electrodes that are on a scale of 10 s of microns which has made manipulation of submicron particles (e.g., nanometer scale particles, such as certain viruses) difficult using an integrated circuit device or process. It is desirable to be able to perform DEP of submicron particles (e.g., viruses) to facilitate detection of such particles. It is also desirable to be able to detect submicron particles in an efficient manner.

Systems, devices, and/or methods are presented that can facilitate efficient electronic manipulation (e.g., employing electrophoresis (EP), DEP, or multiple frequency DEP (MFDEP)) and detection of small scale particles (e.g., nanometer scale particles). It is to be understood that small scale particles in this context refers generally to objects with dimensions equal to or smaller than 1-100 um, (e.g., biological cells) and particularly to objects with dimensions of nanometer scale and below (e.g., viruses, components of viruses, and biological macromolecules. In one aspect, a particle manipulation device can be fabricated and employed to manipulate small scale particles (e.g., submicron scale particles, such as nanometer scale particles) using a process implemented on an integrated circuit(s), for example. The particle manipulation device can comprise an integrated circuit (IC) chip that can be oriented so that handle silicon on the IC chip can be face up, and the metal interconnection layers can be face down. The IC chip can be attached to a suitable support structure (e.g., circuit board, packaging device, ceramic interposer, or another silicon wafer as part of a vertical chip stack). At least a portion of the handle silicon can be removed (e.g., by grinding or other process) from the IC chip so that the active semiconductor layers (e.g., doped silicon or polysilicon) of the chip can be exposed or at least can be closer to the face-up surface of the chip. A plurality of electrodes can be formed on one or more of the active semiconductor layers, which can support the formation of features (e.g., electrode size and electrode-to-electrode separation) at the smallest, or at least a significantly smaller, available dimension (e.g., nanometer scale in size) of an IC fabrication process to facilitate manipulation of small scale particles. In one aspect, the plurality of electrodes can be formed as a large and dense collection of electrodes.

The subject innovation, by forming a large and dense collection of electrodes (e.g., linear electrode array, two-dimensional electrode array, etc.) with such a fine pitch, can yield a high degree of selectivity when manipulating submicron scale particles. This is a large reduction in electrode feature size as compared to conventional DEP-based systems and devices implemented using integrated circuit technologies, which typically form trapping electrodes using the top metal layers of a IC chip that are normally reserved for bonding pads and are typically on a scale ranging from a few microns to tens of microns.

In another aspect, a fluidic chamber(s) can be placed on the face-up surface of the IC chip, where the fluidic chamber(s) can be positioned over the plurality of electrodes to facilitate placing the plurality of electrodes in closer proximity to the fluidic chamber(s). Particles, such as small scale particles, can be placed in a buffer solution, which can be contained in the fluidic chamber(s). One or more voltage waveforms having respective frequencies can be applied to a subset(s) of electrodes to facilitate generating a respective spatially non-uniform electric field(s) that can be applied to the particles to facilitate manipulating the particles (e.g., for various separation and isolation operations) based at least in part on one or more physical properties of respective particles (e.g., size, mass, and/or electrical conductivity), where the particles can be manipulated into desired regions of the fluidic chamber and/or for the formation of specific spatial patterns of particles in the fluidic chamber (e.g., parallel or substantially parallel lines of particles corresponding to a diffraction grating).

In accordance with various embodiments, a lab-on-chip device can comprise the IC chip with the plurality of electrodes and the fluidic chamber(s). The lab-on-chip device can also comprise digital and/or analog electronic components that can facilitate controlling and selecting desired voltage waveforms that can be applied to the electrodes. In one embodiment, the digital and/or analog electronic components can be on the same IC chip as the electrodes. In another embodiment, the digital and/or analog electronic components can be on one or more disparate IC chips of a lab-on-chip device (e.g., 3D integrated circuit), which can comprise a desired number of IC chips (e.g., IC wafers) positioned in a vertically tiered manner, for example. The lab-on-chip can be employed to facilitate efficient manipulation and detection of small scale particles, which can be contained in a buffer solution in the fluidic chamber(s).

In another embodiment, multiple frequencies can be applied sequentially (e.g., in temporal and/or spatial sequences) to disparate electrodes to facilitate manipulating and separating disparate particles based at least in part on the respective physical properties of the disparate particles. The disparate types of particles can be progressively separated from each other and trapped based at least in part on the frequencies respectively applied to the particles.

In accordance with an aspect, with the particles manipulated into a desired formation, such as a diffraction grating, the particles (e.g., disparate types of particles) can be detected (e.g., optically detected) using innovative macro-scale optical detection. A light beam of a specified wavelength (e.g., visible or subvisible light) can be transmitted onto the particles (or a portion thereof), as formed into a diffraction grating (or a portion thereof), to facilitate obtaining an optical readout of optical power of the diffracted light at an angle corresponding to one of the diffraction orders for the diffraction grating. The optical power at the detection angle can be based at least in part on the optical power at the readout wavelength of the incident light beam, the diffraction order selected, and the efficiency of the diffraction grating, where the efficiency of the grated can relate to the density of particles trapped into respective lines of the grating. The optical power of the diffracted light, which can be at a corresponding diffraction angle when diffracted from a region of the spatial grating pattern populated with particles of a particular type, can be measured to facilitate detection and assay of the particles. The measured optical power can be compared to known assays to obtain accurate measurements of particle populations. Thus, the subject innovation can facilitate efficient electronic manipulation of small scale particles, such as submicron scale particles, and detection of the particles using innovative macro-scale optical detection.

FIG. 1 illustrates a diagram of a device 100 that can facilitate electronic manipulation and detection of small scale particles in accordance with an aspect of the disclosed subject matter. In accordance with one aspect, the device 100 can include an IC chip 102 that can comprise a plurality of electrodes 104 that can be formed in a pattern (e.g., a linear array, 2-dimensional or other regular pattern, or an irregular pattern). The plurality of electrodes 104 can be used to facilitate electronically manipulation (e.g., employing DEP) of one or more disparate types of particles (e.g., submicron scale particles, such as nanometer scale particles) that can be contained in a buffer solution that can be inserted into a fluidic chamber(s) 106 (e.g., microfluidic structure(s), channel(s), trench(es) and/or reservoir(s))) formed (e.g., etched). in a fluid containment structure 108, which can be located on the top surface of the device 100.

In one aspect, the fluid containment structure(s) 108 can be formed by removing any or all of the handle silicon (e.g., substrate) from the IC chip 102. In one embodiment, a portion of the handle silicon of the IC chip 102 can be removed (e.g., employing chemical etching techniques) to form the fluidic chamber(s) 106, where the remaining handle silicon can be the fluid containment structure 108. In another embodiment, all or a portion of the handle silicon can be removed from the IC chip 102, and a fluid containment structure 108 can be formed by depositing virtually any of a variety of materials that can be grown on, deposited on, or attached to the surface of the IC chip 102. It is to be appreciated and understood that removal of all or a portion of the handle silicon typically can occur in relation to orienting the IC chip 102 so that the metal layer of the IC chip is face down, such as described herein.

In one aspect, the IC chip 102 can be oriented so that the handle silicon of the IC chip 102 can be face up, where the face-down surface (e.g., the metal interconnection layer(s)) of the IC chip 102 can be fastened (e.g., bonded) to a support structure (e.g., circuit board, packaging device, ceramic interposer, ceramic interposer, another IC chip as part of a vertical chip stack, . . . —not shown) thereunder. In another aspect, at least a portion (e.g., part or all) of the handle silicon can be removed (e.g., removed by grinding) so that the active semiconductor layer(s) 110 can be exposed or at least can be closer to the surface of the IC chip 102, as compared to conventional devices (e.g., lab-on-chip devices).

The active semiconductor layer(s) 110 (e.g., doped silicon or polysilicon) can be the layer(s) of IC chip 102 that can maintain the smallest feature size (or at least a very small feature size) on the IC chip 102 (e.g., components and vias formed on the active semiconductor layer(s) 110 can have the smallest feature size or a substantially smaller feature size as compared to other layers, such as metal layers, of the IC chip 102). A plurality of electrodes 104 can be formed in the active semiconductor layer(s) layer 110, where each of the plurality of electrodes 104 can be formed having a size corresponding to the smallest (or a very small) feature size for the active semiconductor layer(s) 110 of the IC chip 102. For instance, each of the plurality of electrodes 104 can be submicron scale (e.g., nanometer scale) in size (e.g., 180 nm width, 65 nm width, or smaller). In another aspect, the plurality of electrodes 104 (e.g., 2,048 electrodes) can be formed in a large pattern (e.g., linear array; 2-dimensional array; other regular pattern, such as a regular polygonal pattern; an irregular array). In still another aspect, the gap spacing between adjacent electrodes 104 in the array can be on a submicron scale (e.g., 270 nm or smaller gap spacing) to facilitate electronic manipulation of particles.

In still another aspect, the plurality of electrodes 104 can be positioned in close proximity to one or more fluidic chambers 106 (e.g., trench(es)) that can be formed (e.g., etched) in the fluid containment structure 108 (e.g., top surface of the device 100). The fluid containment structure 108 can be fashioned on the face-up surface of the IC chip 102, where the fluidic chamber(s) 106 can be positioned over the plurality of electrodes 104. With the orientation of the IC chip 102, removal of at least a portion of the handle silicon from the IC chip 102, and positioning of the fluidic chamber(s) 106 over the electrodes 104, the plurality of electrodes 104 can be positioned in close proximity to the fluidic chamber(s) 106.

In accordance with another aspect, the fluidic chamber(s) 106 can have a bottom surface that can be constructed of a reflective material or can have a reflective material placed or formed thereon. The reflective bottom surface of the fluidic chamber(s) 106 can facilitate detection (e.g., optical detection) of particles in the buffer solution (e.g., after manipulation of the particles). In accordance with still another aspect, fluidic chambers 106 can be the same or different in size, as desired. One or more fluidic chambers 106 can be utilized for other desired purposes, such as, for example, using a fluidic chamber(s) 106 as a reservoir that contains a relatively large quantity particles contained in a buffer solution, where a desired portion of the particles and buffer solution can be distributed to another fluidic chamber 106 positioned in close proximity to the electrodes 104.

In accordance with an aspect, the device 100 can be utilized to facilitate manipulating small scale particles, such as submicron scale particles. A desired buffer solution can be inserted into the fluidic chamber(s) 106, where there can be particles of interest (e.g., submicron scale particles, such as nanometer scale particles) contained in the buffer solution. In an aspect, an electrokinetic technique, such as, for example, EP, DEP, and/or MFDEP, can be employed to facilitate arranging particles into a defined spatial pattern. Specified voltage waveforms can be applied to a subset(s) of the electrodes 104 to facilitate generating a spatially nonuniform electric field(s) having a specified frequency(ies) that can be utilized to apply a corresponding force on the particles of interest, which can be one or more disparate types of particles, to manipulate (e.g., move particles, sort disparate types of particles, separate disparate types of particles) and trap the particles without having to come in direct contact with the particles. Placing the electrodes 104 in close proximity to the fluidic chamber(s) 106, along with the submicron scale of the electrodes 104 (e.g., 180 nm width or smaller) and submicron scale of the gap spacing (e.g., 270 nm or smaller gap spacing) between adjacent electrodes 104 in the linear electrode array, can facilitate optimizing (e.g., maximizing) the electric field strength(s), which can facilitate electronic manipulation (e.g., DEP) and detection of submicron particles contained in the buffer solution in the fluidic chamber(s) 106.

In accordance with another aspect, device 100 can comprise one or more covers (not shown) that can be placed on the one or more fluidic chambers 106, as desired, to cover the opening of a fluidic chamber(s) 106 to facilitate improving the strength of an electric field generated and applied to particles in the fluidic chamber(s) 106. For example, the cover(s) can comprise a planar electrode(s) (not shown) that can facilitate providing an even ground plane. The cover can modify an electric field so that the electric field can be between adjacent electrodes 104 and the planar electrode, which can improve the electric field strength in the fluidic chamber(s) 106, as opposed to the resulting electric field between adjacent electrodes 104 when no cover is employed. The cover also can improve controlling manipulation of particles in the fluidic chamber(s) 106. In an embodiment, a cover(s) can comprise a plurality of planar electrodes that can be formed into a desired defined pattern (e.g., linear array, two dimensional array, regular pattern, irregular pattern), which can further improve electric field strength and control of manipulation of particles.

It is to be appreciated and understood that, in accordance with various embodiments, the voltage waveforms provided to the electrodes 104 can be from electronic components (not shown) on IC chip 102, one or more other IC chips (not shown in FIG. 1) with components formed thereon to facilitate providing the voltage waveforms to the electrodes 104, an integrated circuit on a printed circuit board(s) (not shown in FIG. 1) with components contained thereon to facilitate providing the voltage waveforms to the electrodes 104, and/or other components that can facilitate providing the voltage waveforms to the electrodes 104.

In another aspect, through electronic manipulation of the particles (e.g., by employing DEP), the device 100 can arrange and trap particles in the form of a defined spatial pattern to facilitate detection and assay of the one or more types of particles, where respective particles can be arranged based at least in part on the respective physical properties, such as size, mass, and dielectric properties (e.g., permittivities, conductivities), of the particles. For example, there can be a mixture of particles comprising a first type of particle and a second type of particle. The mixture of particles can be placed in a buffer solution, where the buffer solution can be placed in a fluidic chamber 106 of device 100. The first type of particle can have a first set of physical properties, and the second type of particle can have a second set of physical properties.

A first subset of electrodes 104 (e.g., one or more electrodes 104) can receive a first voltage waveform (e.g., sine wave) at a first frequency and first magnitude, and a first electric field (e.g., first spatially nonuniform electric field) can be generated and applied to the particles in the fluidic chamber 106. A second subset of electrodes 104 can receive a second voltage waveform at a second frequency and second magnitude, and a second electric field (e.g., second spatially nonuniform electric field) can be generated and applied to the particles in the fluidic chamber 106. Based at least on the first set of physical properties and the first frequency, the first type of particles can be attracted to the first subset of electrodes 104. As a result, the first type of particles can move to a region in the fluidic chamber 106 near the first subset of electrodes 104 and can become trapped as the first type of particles can be attracted to the electric-field maxima associated with the first electric field, while the second type of particles can move away from the region in the fluidic chamber 106 near the first subset of electrodes 104. Based at least on the second set of physical properties and second frequency, the second type of particles can be attracted to the second subset of electrodes 104. As a result, the second type of particles can move to a region in the fluidic chamber 106 near the second subset of electrodes 104 and can become trapped as the second type of particles can be attracted to the electric-field maxima associated with the second electric field. It is to be appreciated and understood that device 100 can facilitate manipulation of more than two types of particles as desired.

In accordance with yet another aspect, the device 100 can be utilized to employ sequential application of multiple frequencies (e.g., in temporal and/or spatial sequences) to facilitate manipulating disparate types of particles to arrange and trap the particles as desired. For instance, disparate types of particles can be contained in a buffer solution placed in a fluidic chamber 106. A first voltage waveform having a first frequency can be applied to a first subset of electrodes 104 to generate a first electric field (e.g., first spatially nonuniform electric field). A first force, based at least in part on the first electric field, can be applied to the disparate types of particles where at least a first subset of particles can be manipulated so they are separated from other particles and trapped in a region of the fluidic chamber 106 near the first subset of electrodes 104 based at least in part on the first frequency and the physical properties of the first subset of particles (e.g., the first subset of particles can form a diffraction line that can correspond to the layout of the first subset of electrodes 104).

A second voltage waveform having a second frequency can be selected and applied to a second subset of electrodes 104 to facilitate manipulating a second subset of particles to separate them from other particles and trap the second subset of particles in a region in the fluidic chamber 106 near the second subset of electrodes. As desired, one or more additional voltage waveforms of respective frequencies can be applied to one or more additional subsets of electrodes 104 to facilitate manipulating the particles so the particles in the fluidic chamber 106 can be separated and arranged into a desired spatial pattern based at least in part on the frequencies applied and respective physical properties of the particles.

It is to be appreciated and understood that the particles can be manipulated, arranged, and trapped in any of a variety of different ways, as desired. For example, disparate particles in the buffer solution can be manipulated by applying a voltage waveform of a first frequency to a first subset of electrodes to facilitate bifurcating the particles into two groups based at least in part the first frequency and respective physical properties of the particles. One or more other voltage waveforms having respective frequencies can be applied to one or both of the two groups of particles to bifurcate the two groups of particles (or only one of the two groups, as desired) into more refined groups of particles based at least in part on the respective frequency(ies) of the other waveform(s) and physical properties of respective particles. As desired, the bifurcation process can continue until the particles are separated and arranged into a desired spatial pattern to facilitate detection of the particles. For example, the particles can be arranged into a diffraction grating, where there can be one or more grating lines for each type of particle (e.g., one or more grating lines for a first type of particle, one or more grating lines that contain a second type of particle, . . . ). Such a diffraction grating can facilitate detecting and assaying the respective particles.

Figure 2A:
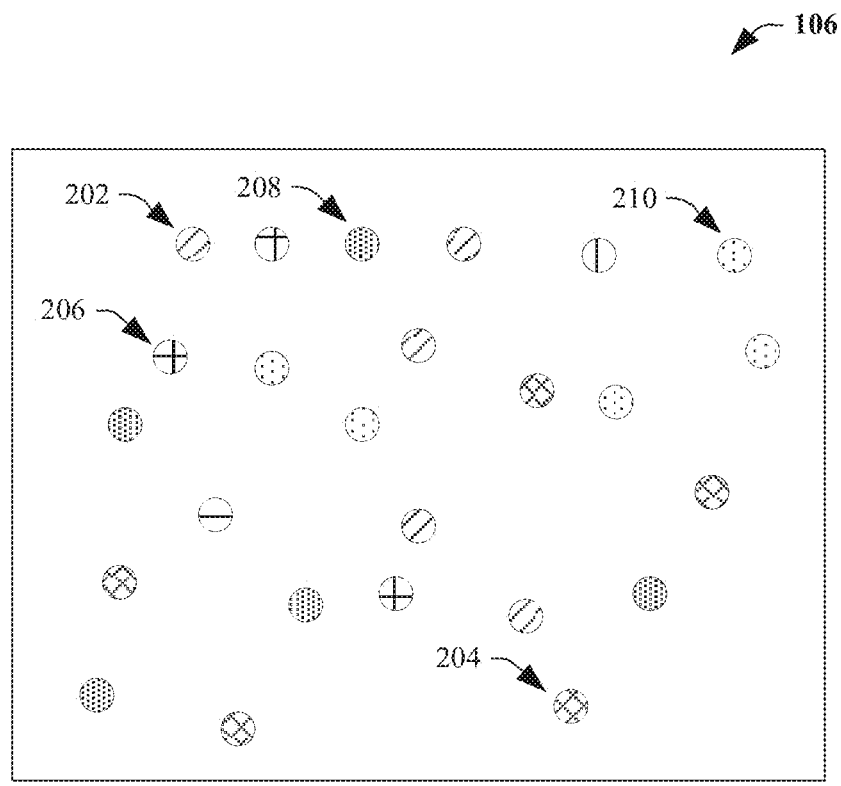
FIGS. 2A-2D illustrates diagrams of example manipulation of small scale particles in response to the application of multiple frequencies in accordance with an aspect of the disclosed subject matter.

Turning briefly to FIGS. 2A-2D, illustrated is an example of employing DEP to facilitate electronic manipulation of disparate types of particles (e.g., herpes simplex virus-1 (HSV-1) capsids). FIG. 2A is an illustrative diagram of an example portion of a fluidic chamber 106 that can contain disparate types of particles contained in a buffer solution in the fluidic chamber 106. As depicted in FIG. 2A, the disparate particles can be randomly positioned in the buffer solution in the fluidic chamber 106 prior to the electronic manipulation being performed. For this example, there are five different types of particles: particles 202, particles 204, particles 206, particles 208, and particles 210. It is to be appreciated and understood that the subject innovation is not limited to manipulating and separating five particle types, as the subject innovation can facilitate manipulating and separating less than five disparate types of particles, five disparate types of particles, or more than five disparate types of particles, as desired.

Figure 2B:
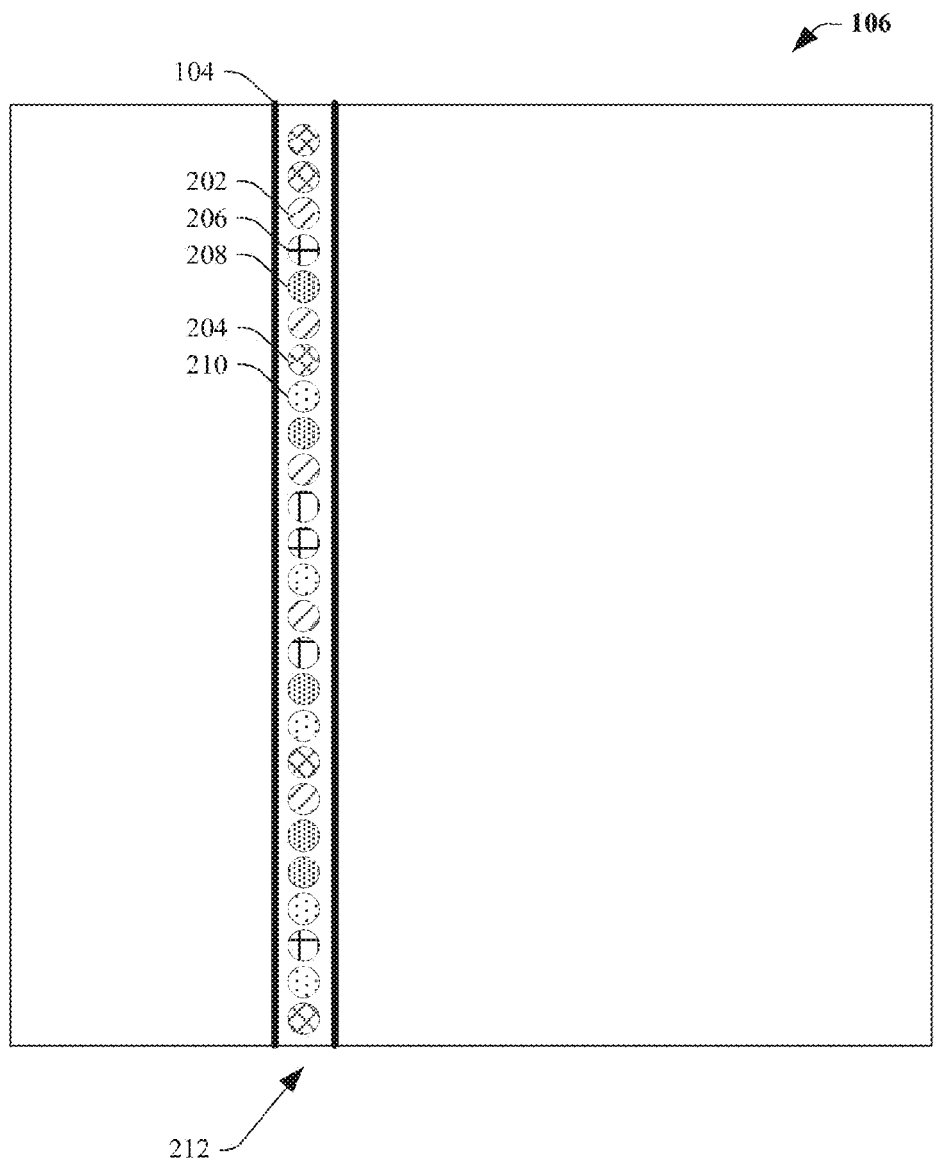

FIG. 2B depicts an illustrative diagram of the example portion of the fluidic chamber 106 with the disparate types of particles in the buffer solution when a first voltage waveform having a first frequency is applied to a first subset of electrodes 104 to facilitate manipulating the particles. The first voltage waveform with the first frequency (e.g., 4 MHz) can be applied to a subset of electrodes 104 which can generate a first electric field (e.g., spatially nonuniform electric field) where the force of the electric field can attract and trap the disparate types of particles 202, 204, 206, 208, 210 (e.g., in a DEP trap) to a location in the fluidic chamber 106 near the first subset of electrodes 104, based at least in part on the first frequency and the respective physical properties of the particles 202, 204, 206, 208, 210, as depicted at reference numeral 212. It is to be appreciated and understood that, with regard to FIGS. 2B, 2C, and 2D, there can be a plurality of electrodes 104 in close proximity to the fluidic chamber 106, however, for clarity, only selected subsets of electrodes 104 having respective voltage waveforms applied thereto are shown.

Figure 2C:
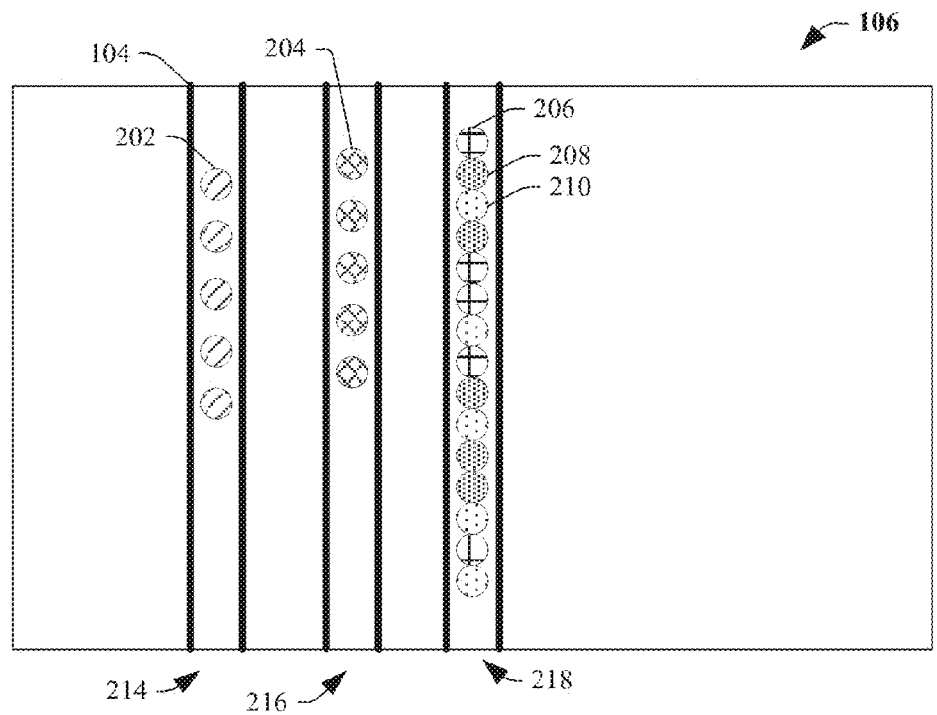

FIG. 2C depicts an illustrative diagram of the example portion of the fluidic chamber 106 with the disparate types of particles in the buffer solution when a second voltage waveform having a second frequency is sequentially applied to a second subset of electrodes 104 to facilitate further manipulating the particles. The second voltage waveform with the second frequency (e.g., 4.6 MHz) can be applied to the second subset of electrodes 104 which can generate a second electric field (e.g., spatially nonuniform electric field) where the force of the second electric field (and the first electric field) can facilitate trapping two types of disparate particles 202 and 204 based at least in part on the second frequency and the respective physical properties of particles 202 and 204 (e.g., particle 202 can have a conductivity of 33.0e-3 $Sm^{-1}$, and particle 204 can have a conductivity of 31.5e-3 $Sm^{-1}$), and the remaining disparate particles 206, 208, and 210 can move to local minima on the right, as depicted at reference numerals 214, 216 and 218, respectively.

Figure 2D:
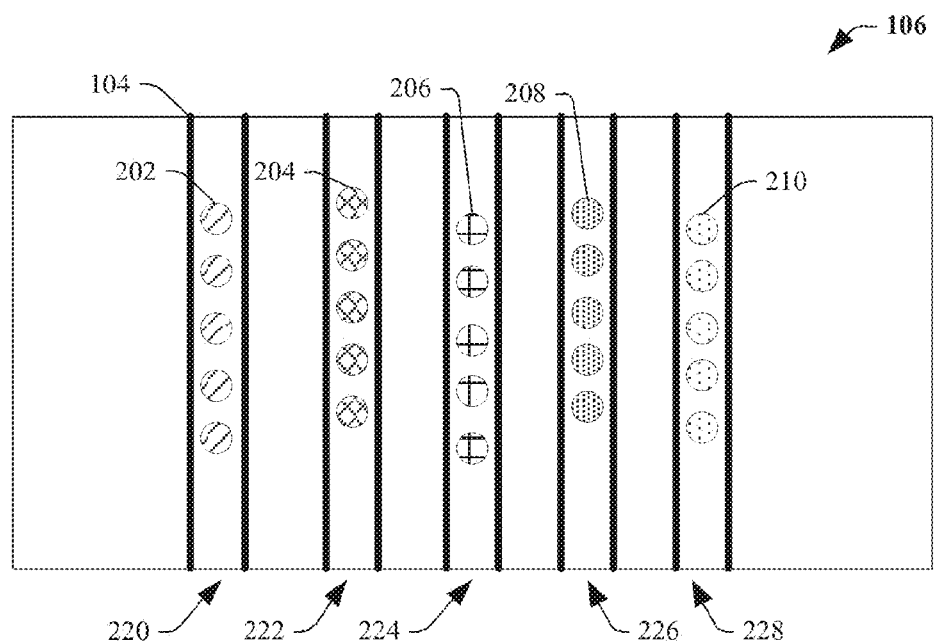

FIG. 2D depicts an illustrative diagram of the example portion of the fluidic chamber 106 with the disparate types of particles in the buffer solution after five voltage waveforms having five respective frequencies are sequentially applied to respective subsets of electrodes 104 to facilitate further manipulating and trapping the particles. A third voltage waveform with the third frequency (e.g., higher than 4.6 MHz) can be applied to a third subset of electrodes 104 which can generate a third electric field (e.g., spatially nonuniform electric field) where the force of the third electric field can attract and trap particles 206 based at least in part on the third frequency and the physical properties of particles 206 (e.g., particle 206 can have a conductivity that is lower than the particles 202 and 204), and the remaining disparate particles 208 and 210 can move to local minima on the right.

A fourth voltage waveform with the fourth frequency (e.g., higher than the third frequency) can be applied to a fourth subset of electrodes 104 which can generate a fourth electric field (e.g., spatially nonuniform electric field) where the force of the fourth electric field can attract and trap particles 208 based at least in part on the fourth frequency and the physical properties of particles 208 (e.g., particle 208 can have a conductivity that is lower than the particles 202, 204, and 206), and the remaining particles 210 can move to local minima on the right. A fifth voltage waveform with the fifth frequency (e.g., higher than the fourth frequency) can be applied to a fifth subset of electrodes 104 (not shown in FIG. 2D) which can generate a fifth electric field (e.g., spatially nonuniform electric field) where the force of the fifth electric field can attract and trap particles 210 based at least in part on the fifth frequency and the physical properties of particles 210 (e.g., particle 210 can have a conductivity that is lower than the particles 202, 204, 206, and 208). The result can be fully fractionated mixture in five DEP traps, where the particles 202, 204, 206, 208, and 210 can be fractionated in order of decreasing conductivity, as depicted at reference numerals 220, 222, 224, 226, and 228, respectively.

It is to be appreciated and understood that while only one line (e.g., diffraction grating line) of particles is depicted with regard to each type of particle, the subject innovation is not so limited as there can be more than one line dedicated to a particular type of particle. For example, the particles 202, 204, 206, 208, and 210 can be manipulated (e.g., using device 100) so that there can be more than one line of particles 202, more than one line of particles 204, more than one line of particles 206, more than one line of particles 208, and/or more than one line of particles 210, as desired. Having more than one line of a particular type of particle can facilitate detecting and identifying that particle when there are a sufficient number of that type of particle to support multiple lines. It is to be further appreciated and understood that particles can be formed into virtually any desired spatial pattern. For example, particles can be manipulated into a linear pattern, such as a diffraction grating, a two-dimensional pattern or other regular pattern, an irregular or a nonuniform pattern.

Referring again to FIG. 1, in accordance with another aspect, device 100 can be utilized to employ multiple frequencies at the same time to facilitate manipulating particles contained in a buffer solution in a fluidic chamber 106 based at least in part on the respective frequencies and the respective physical properties of the particles. For instance, one voltage waveform having a first frequency can be applied to a first subset of electrodes 104 and a second voltage waveform having a second frequency can be applied to a second subset of electrodes 104 at the same time to facilitate manipulating the particles based at least in part on the first and second frequencies and the respective physical properties (e.g., electrical conductivity) of the particles.

In accordance with an embodiment of the subject innovation, after the particles are manipulated to arrange and trap the particles as desired (e.g., particles are trapped to arrange a diffraction grating), the trapped particles can be detected, for example, using innovative macro-scale optical detection, such as more fully described herein.

Figure 3:
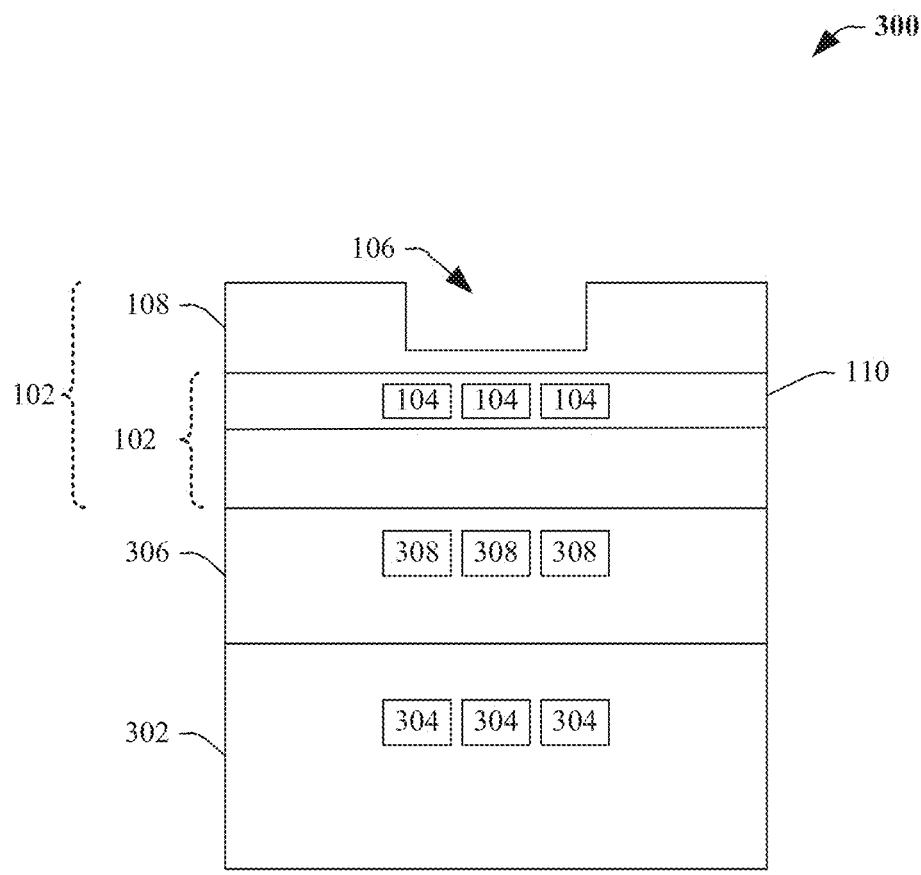
FIG. 3 depicts a diagram of a device that can facilitate electronic manipulation and detection of small scale particles in accordance with an aspect of the disclosed subject matter.

Referring to FIG. 3, illustrated is a diagram of a device 300 that can facilitate electronic manipulation and detection of small scale particles in accordance with an aspect of the disclosed subject matter. Device 300 (e.g., lab-on-chip) can include an IC chip 102 (e.g., also referred to as third IC chip 102 with regard to device 300) on which a plurality of electrodes 104 can be formed. A fluid containment structure 108 can be placed over the plurality of electrodes 104 and IC chip 102. A fluidic chamber(s) 106 can be formed in the fluid containment structure 108, where the fluidic chamber(s) 106 can be formed over the plurality of electrodes 104. The IC chip 102, plurality of electrodes 104, fluidic chamber(s) 106, and fluid containment structure 108, each can be the same or similar as, and/or can comprise the same or similar functionality as, respective components such as more fully described herein, for example, with regard to device 100.

In one aspect, device 300 also can include a first IC chip 302 that can be placed at the bottom of a vertical chip stack. The first IC chip 302 can comprise a plurality of control components 304 formed thereon that can facilitate selecting a desired voltage waveform that can be applied to corresponding electrodes 104 associated with the control components 304. In accordance with one embodiment, the plurality of control components 304 can be digital control components, such as digital shift registers (e.g., circular shift registers). For example, if four waveforms are utilized with the electrodes 104, a 2-bit wide, 4-bit deep circular shift register can be employed as a control component 304. The first IC chip 302 also can comprise handle silicon (not separately shown and identified in FIG. 3) in the bottom region of the silicon wafer 302.

In another aspect, a second IC chip 306 can comprise a plurality of selector components 308 formed thereon that can be used to facilitate selecting a desired waveform of a predefined number of different voltage waveforms that can be applied to corresponding electrodes 104 to facilitate manipulating particles (e.g., particles in a buffer solution in a fluid channel(s) 106). In one aspect, the voltage waveforms can be provided to the selector components 308 externally or the voltage waveforms can be generated by device 300. In one embodiment, the orientation of the second silicon wafer 306 optionally can be re-arranged such that the handle silicon region of the second IC chip 306 can be face up and the surface where the metal interconnection layers are located can be face down (e.g., second IC chip 306 can be turned upside down), as compared to conventional orientation of IC chips, and the second IC chip 306 can be adhered (e.g., bonded) to the top surface of the first IC chip 302, where the second IC chip 306 is positioned above the first IC chip 302 in the vertical chip stack. In another aspect, optionally, at least a portion of the handle silicon can be removed from the second silicon wafer 306. In another embodiment, the handle silicon surface of the second IC chip 306 can be bonded to the top surface of the first IC chip 302 in the vertical chip stack. In an aspect, the plurality of control components 304 can be connected to corresponding selector components 308 to facilitate controlling selection and application of the desired voltage waveform to a corresponding electrode 104 to facilitate manipulating particles.

In accordance with an embodiment, each of the plurality of selector components 308 can be an analog multiplexer (mux) (e.g., 4:1 analog multiplexer, if 4 voltage waveforms are employed) that can receive the predefined number of voltage waveforms at the input of the multiplexer and can provide one of those voltage waveforms as the selected voltage waveform, which can be output to the corresponding electrode 104 connected therewith.

In accordance with an aspect of the disclosed subject matter, the third IC chip 102 can be oriented so that the handle silicon region of the IC chip 102 can be facing up, and the face-down surface (e.g., having metal interconnection layers) of the third IC chip 102 can be adhered to the second IC chip 304 in the vertical chip stack. As a result, the active semiconductor layers 110 of the third IC chip 102, which can comprise the plurality of electrodes 104, can be in closer proximity to the fluidic chamber(s) 106 of the fluid containment structure 108, which can be adhered to the third IC chip 102 in the vertical chip stack.

In accordance with an aspect, the device 300 can be utilized to facilitate manipulating (e.g., employing EP, DEP, and/or MFDEP) small scale particles (e.g., one or more disparate types of particles), such as submicron scale particles (e.g., nanometer scale particles). A desired buffer solution can be inserted into the fluidic chamber(s) 106, where there can be particles of interest (e.g., submicron scale particles, such as nanometer scale particles) contained in the buffer solution.

The device 300 can be placed in circulation mode where a subset of control components 304 can provide signals to corresponding subset of selector components 308 to facilitate producing a time sequence pattern for applying the voltage waveforms to a corresponding subset of electrodes 104. The specified voltage waveforms applied to the desired electrodes 104 in the time sequence pattern (e.g., selecting a different voltage waveform to be applied to a desired subset of electrodes 104 on the rising edge of each clock cycle) can facilitate generating a spatially nonuniform electric field(s) that can be utilized to apply a force(s), which can correspond to the respective electric field(s), on the particles of interest to manipulate and trap the particles, or a subset thereof, without having to come in direct contact with the particles. Placing the electrodes 104 in close proximity to the fluidic chamber(s) 106, along with the submicron scale of the electrodes 104 (e.g., 180 nm or smaller width) and submicron scale of the gap spacing (e.g., 270 nm or smaller gap spacing) between adjacent electrodes 104 in the linear electrode array, can facilitate optimizing (e.g., maximizing) the electric field strength, which can facilitate electronic manipulation and detection of submicron particles contained in the buffer solution in the fluidic chamber(s) 106. When the particles are manipulated to be arranged in a desired formation (e.g., particles are trapped and arranged to form a diffraction grating), the trapped particles can be detected, for example, using innovative macroscale optical detection, such as more fully described herein (e.g., system 1100, methodology 1500).

In accordance with one embodiment, device 300 can be a three-dimensional chip stack that can be comprised of the fluid containment structure 108, the third IC chip 102 (e.g., third tier), the second IC chip 306 (e.g., second tier), and the first IC chip 302 (e.g., first tier), wherein the topmost tier, the third IC chip 102, can comprise an active semiconductor layer(s) 110 with an array of electrodes 104 formed thereon. The voltage (e.g., voltage waveforms) on each electrode 104 can be individually driven by analog circuitry (e.g., selector components 308) contained in the second IC chip 306. The first IC chip 302 can include a plurality of control components 304 (e.g., digital circuits comprising circular shift registers) that can send signals to corresponding selector components 308 to facilitate selecting a desired voltage waveform for each electrode 104 at a desired time.

In one aspect, with regard to the fluid containment structure 108, two 1,000 um×200 um pad cuts can be made through the fluid containment structure 108 (e.g., over-glass layer), located on the surface of the chip. For instance, the areas of top level metal, which normally are used for contact pads, can be etched (e.g., chemically etched) away within this region to form trenches, which can be fluidic chamber(s) 106. The fluidic chamber(s) 106 can be utilized to hold a buffer solution that contains particles of interest (e.g., submicron scale particles, such as certain viruses). As the third IC chip 102 is oriented and assembled upside down, and at least a portion of its handle silicon is removed, the active semiconductor layer(s) 110 comprising the plurality of electrodes 104 can be located in very close proximity to the fluidic chamber(s) 106. As a result, the active semiconductor layer(s) 110 of the third IC chip 102 can be used to create efficient DEP trapping electrodes (e.g., electrodes 104). Whereas, conventionally the active semiconductor layer(s) is used as interconnect for active circuit devices because the active semiconductor layer(s) would be at the bottom region of the IC chip.

In another aspect of the embodiment, the plurality of electrodes 104 can comprise 2,048 electrodes (e.g., DEP electrodes), formed in a linear array on the active semiconductor layer 110 (e.g., polysilicon layer) of the IC chip 102. Each of the electrodes 104 can be 180 nm wide (or smaller) and 200 um long, where the plurality of electrodes 104 can be situated under the fluidic chamber area (e.g., trench area) with a center to center pitch of 450 nm and an electrode gap spacing of 270 nm (or smaller). The plurality of electrodes 104 can be separated from the bottom surface of the fluidic chamber(s) 106 by 650 nm of oxide (not shown).

In another aspect, the first IC chip 302 can comprise a plurality of control components 304, where each control component 304 can comprise a control register for each of the 2,048 electrodes. Each control register can be utilized to facilitate selecting among four source waveforms (e.g., voltage waveforms) that can be provided to the device 300 from an external source or can be provided by the device 300. The control components 304, which can comprise digital circuitry, can facilitate controlling corresponding selector components 308 of the second IC chip 306, where the selector components 308 can comprise analog circuitry. The select input of each selector component 308, which can be an analog mux (e.g., 4:1 analog mux), can be driven by a corresponding control component 304, which can be a 2-bit wide, 4-bit deep circular shift register. The shift registers can have two modes, load and circulate. To facilitate minimizing the number of input/output (I/O) pins necessary for loading, the output of the last shift register in each row of shift registers can be fed to the input of the subsequent row of shift registers. Once the time sequenced pattern for each row of shift registers has been initialized and the chip placed into circulation mode, the signal on an electrode 104 can switch between one of four analog inputs on each clock cycle. The subject innovation provides desirable flexibility for post-fabrication modification and/or experimentation, as the voltage waveforms are not limited to voltage waveforms generated on the device 300, as other external voltage waveforms can be supplied to the device 300, as desired.

It is to be appreciated and understood that, while device 300 is described with regard to three tiers (e.g., third IC chip 102, second IC chip 306, and first IC chip 302) in the vertical chip stack, the subject innovation is not so limited as there can be virtually any number of IC chips employed in accordance with the disclosed subject matter. For example, in accordance with the disclosed subject matter, device 300 can comprise less than three IC chips, three IC chips, or more than three IC chips, as desired.

Figure 4:
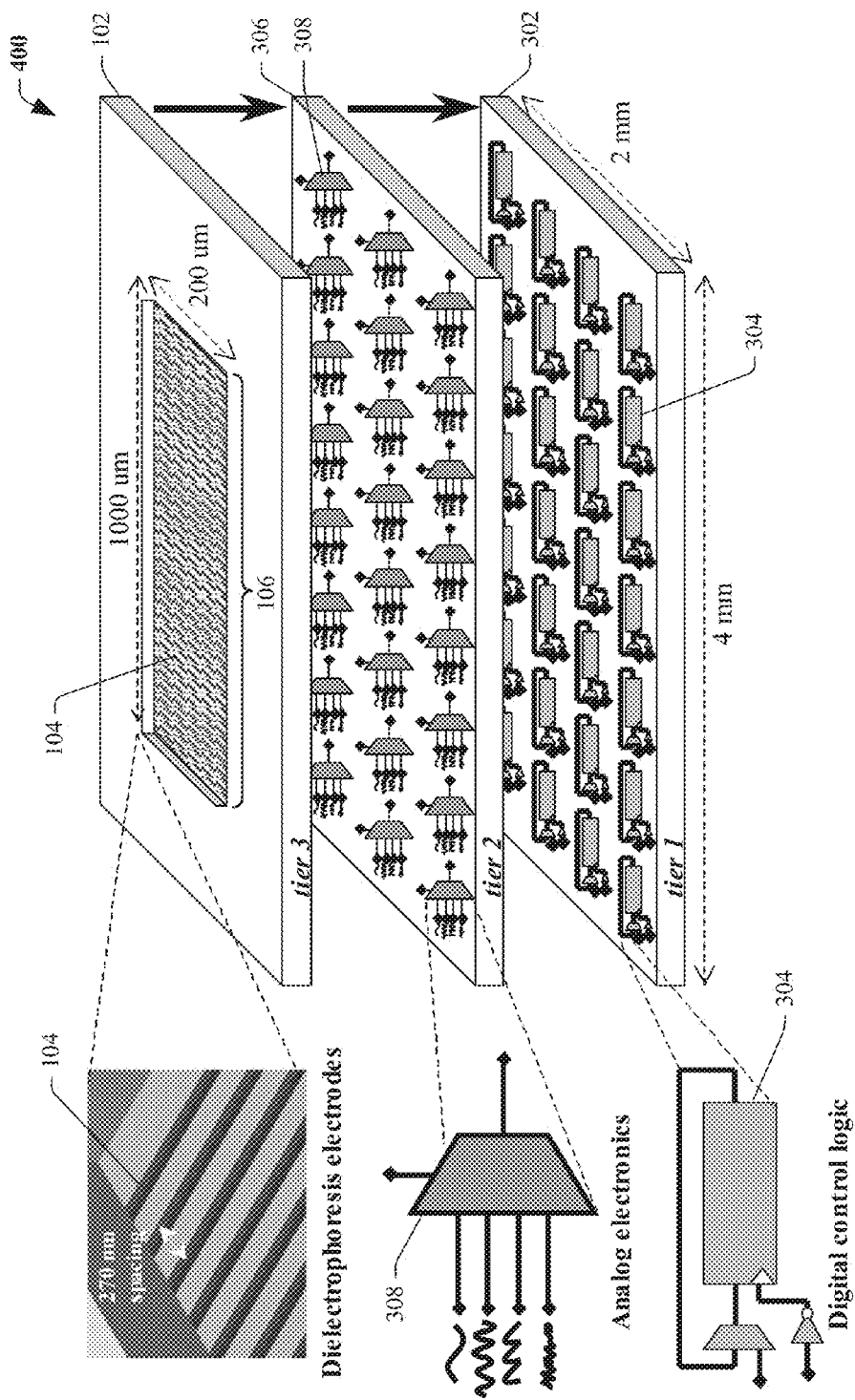
FIG. 4 depicts a diagram of an example lab-on-chip device that can facilitate electronic manipulation and detection of small scale particles in accordance with an embodiment of the disclosed subject matter.

FIG. 4 illustrates a diagram of an example device 400 that can facilitate electronic manipulation and detection of small scale particles in accordance with an embodiment of the disclosed subject matter. Device 400 can comprise a IC chip 102 (e.g., also referred to as third IC chip 102) that can contain a plurality of electrodes 104, a fluidic chamber(s) 106, a fluid containment structure 108, an active semiconductor layer(s) 110, a first IC chip 302, a plurality of control components 304, a second IC chip 304, and a plurality of selector components 308. The IC chip 102, plurality of electrodes 104, fluidic chamber(s) 106, fluid containment structure 108, active semiconductor layer(s) 110, first IC chip 302, plurality of control components 304, second IC chip 304, and plurality of selector components 308, each can be the same or similar as, and/or can comprise the same or similar structure and/or functionality as, respective components such as more fully described herein, for example, with regard to device 100 and/or device 300.

In accordance with an embodiment, the IC chips 102, 302, and 306 each can be 4 mm in length and 2 mm in width. The fluid chamber 106 can be 1000 um in length and 200 um in width. The gap spacing between adjacent electrodes 104 in the linear electrode array can be 270 nm. It is to be appreciated and understood that the aforementioned dimensions are exemplary, and the subject innovation is not so limited, as, in accordance with various embodiments, the respective dimensions can be smaller than or larger than the aforementioned dimensions. For example, the gap spacing between adjacent electrodes can be smaller than 270 nm, such as 65 nm, as desired. The subject innovation can facilitate electronic manipulation and detection of small scale particles, which can be contained in a buffer solution that can be placed in the fluidic chamber 106.

Figure 5:
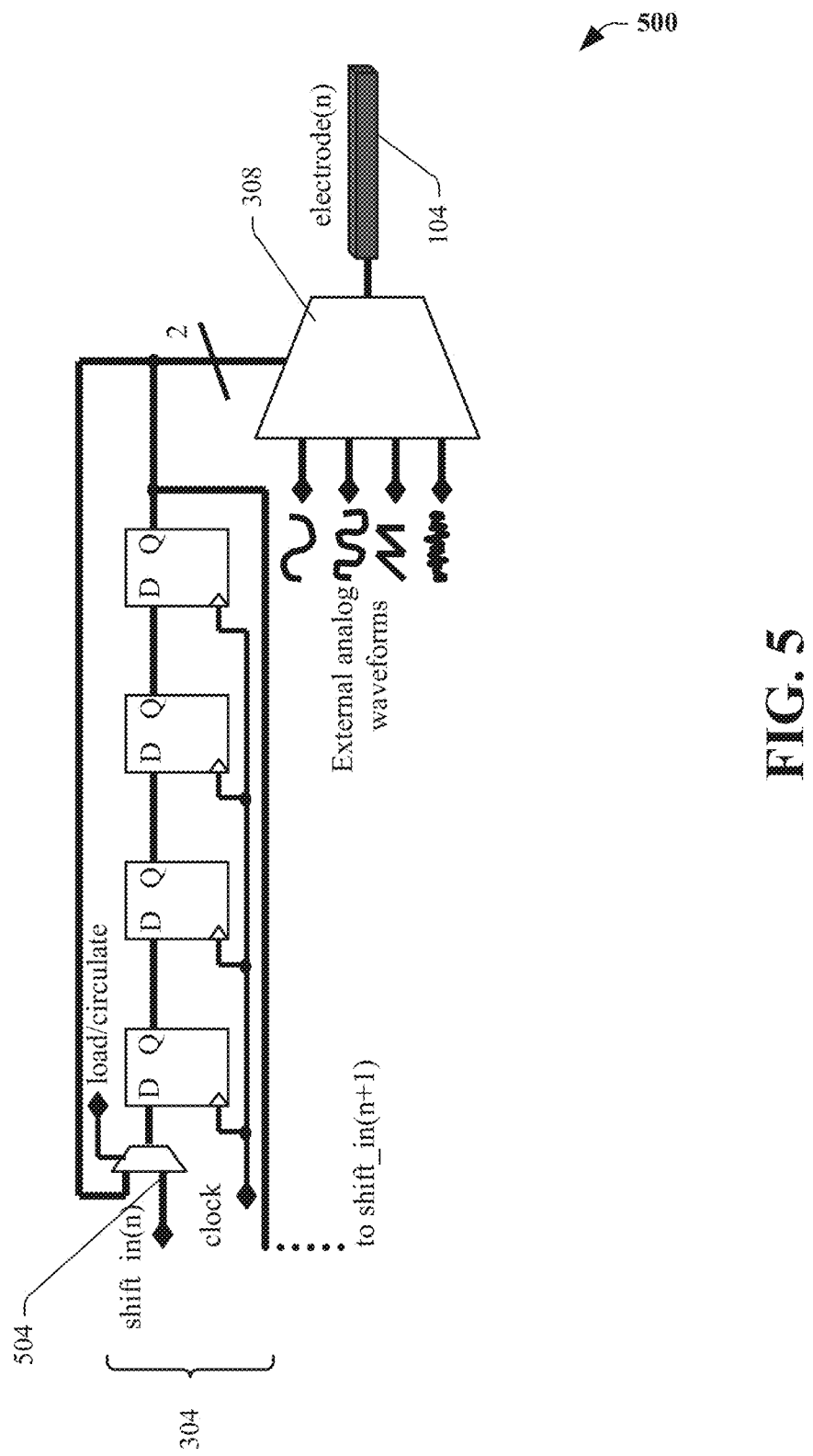
FIG. 5 illustrates an example block diagram of a system that can facilitate providing a desired voltage waveform to an electrode(s) associated with a lab-on-chip in accordance with an embodiment of the disclosed subject matter.

FIG. 5 depicts an example block diagram of a system 500 that can facilitate providing a desired voltage waveform to an electrode(s) associated with a lab-on-chip in accordance with an embodiment of the disclosed subject matter. System 500 can include a control component 304 that can comprise a predetermined number of flip-flop components 502 that can be connected together to form a circular shift register. For example, the number of flip-flop components 502 employed can be based at least in part on the number of voltage waveforms that can be applied to an associated electrode 104 (e.g., four flip-flop components 502 to facilitate selecting between four voltage waveforms). The control component 304 also can include a mux component 504 (e.g., analog mux) that can facilitate selecting between a load mode and circulate mode. The control component 304 can be connected to the selector inputs of a selector component 308, which can be connected to an electrode 104 connected thereto. The selector component 308 can receive as input a predetermined number of voltage waveforms, where one of the voltage waveforms can be selected and provided as an output to the electrode 104 based at least in part on the signals received at the selector inputs of the selector component 308. The voltage waveforms can be received from another component of a lab-on-chip associated therewith or an external component, as desired.

In accordance with another aspect, the output of the control component 304 (e.g., output of the shift register of the control component 304) can be provided to the input of another control component 304 (e.g., input of a shift register of control component 304) (not shown) on a successive row of control components 304 (not shown) when initializing a selection pattern for the voltage waveforms. It is to be appreciated and understood that, while four voltage waveforms and four flip-flop components 502 are depicted in system 500, the subject innovation is not so limited, as in accordance with the subject innovation, there can be less than four voltage waveforms and flip-flop components 502 employed, four voltage waveforms and flip-flop components 502 employed, or more than four voltage waveforms and flip-flop components 502 employed, as desired.

Figure 6:
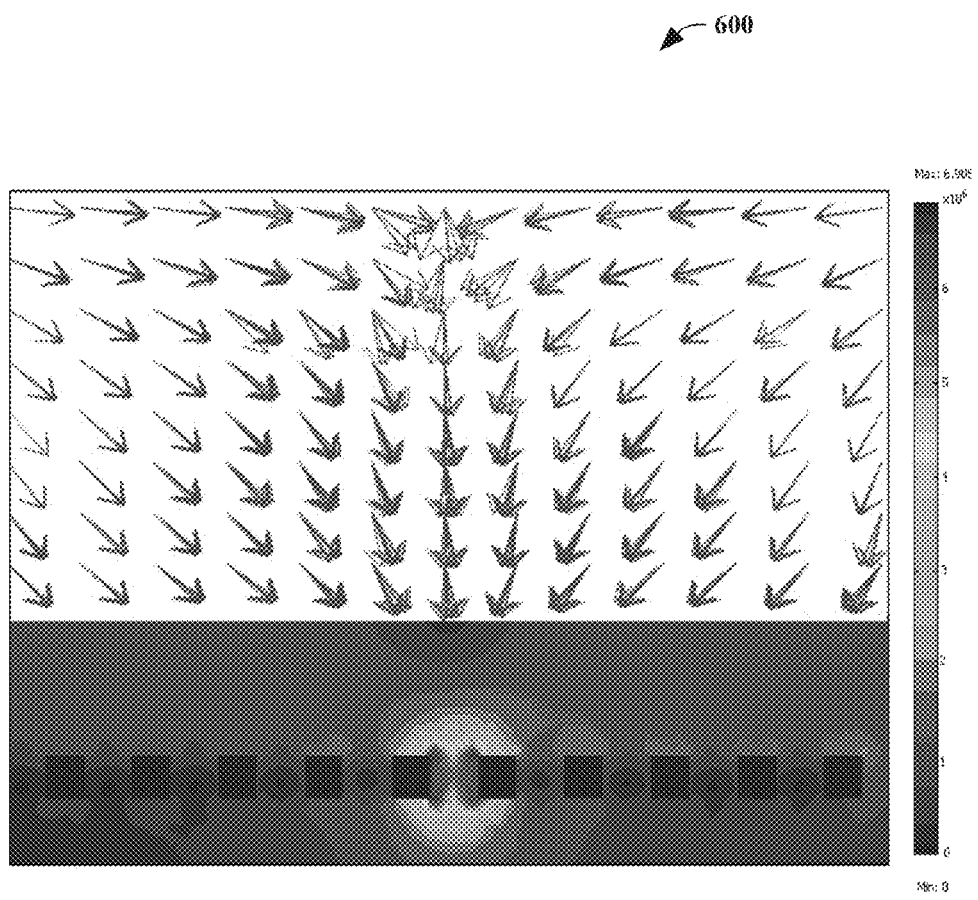
FIG. 6 illustrates a diagram that illustrates example results of a 2D finite-element analysis of the electric field generated within the fluidic trench by the electrodes and the resultant dielectrophoretic forces that act on the particles.

FIG. 6 is a diagram that illustrates example results 600 of a 2D finite-element analysis of the electric field generated within the fluidic trench (e.g., 106) by the electrodes and the resultant dielectrophoretic forces that act on the particles. In this simulation, the first five electrodes, starting from the left hand side of FIG. 6, are assigned a magnitude of 1.5V. The voltages on the remaining electrodes, on the right hand side of FIG. 6, are set 180° out of phase with respect to the other electrodes. This creates an electric field maxima between the $5^{th}$ and $6^{th}$ electrode. The arrows in FIG. 6 show the direction of the dielectrophoretic forces that act on the particles as a function of their location within the trench. For this simulation, the particles are more polarizable than their surrounding medium, yielding a positive value for $Re[K_{cm}]$ and the particles within the buffer solution are attracted towards the electric-field maxima. Experimental results show that when HSV virions are placed in a mannitol solution with a conductivity of 5 mSm$^{-1}$, the particles will transition from undergoing positive to negative DEP in the frequency in the range of 4-5 MHz.

Figure 7A:
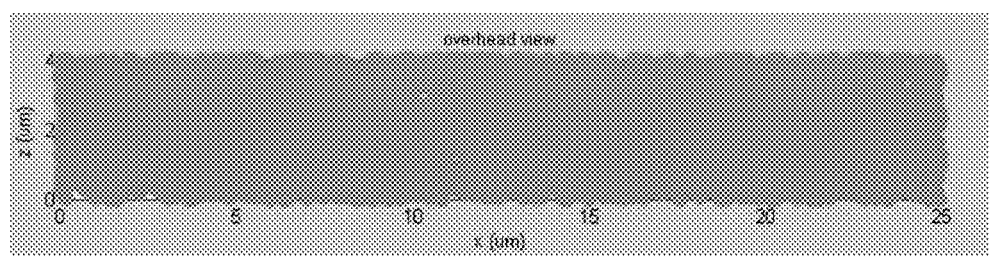
FIGS. 7A-7D illustrate the example results of a simulation of electronic manipulation of virions in a fluidic trench in accordance with an aspect of the disclosed subject matter.
Figure 7B:
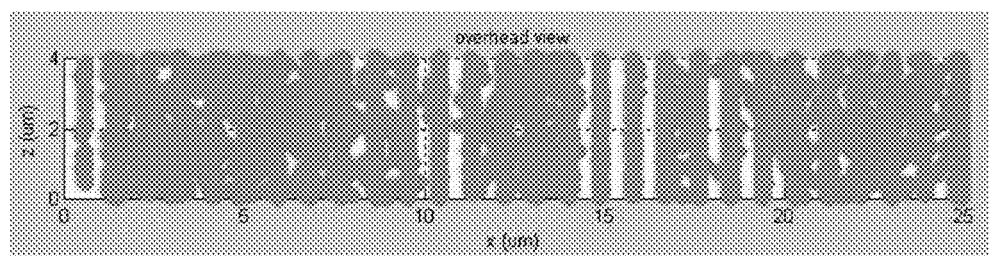
Figure 7C:
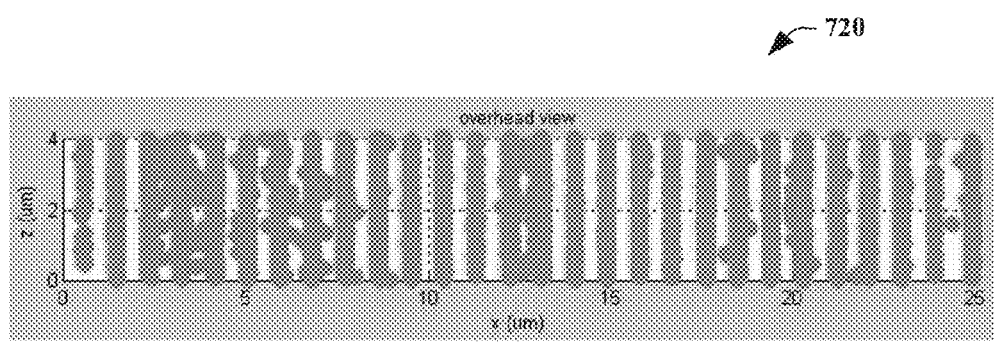
Figure 7D:
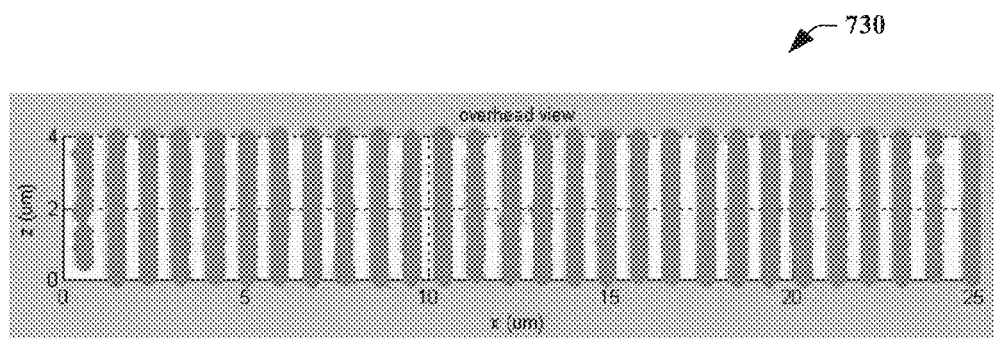

In accordance with an aspect of the disclosed subject matter, FIGS. 7A through 7D illustrate the results of a simulation of electronic manipulation of virions (e.g., particles) in a fluidic chamber (e.g., fluidic chamber 106), where a large concentration of virions are randomly placed in a 4 um×25 um area of the fluidic trench. The voltages are set such that each electrode (e.g., 104) is 180° out of phase with respect to its two neighboring electrodes, creating an alternating pattern of electric field minima and maxima along the bottom surface of the fluidic trench. The results of the finite element analysis shown in FIG. 6 are back annotated into a particle motion simulator and the movement of the virions while under the influence of hydrodynamic drag forces is observed. FIG. 7A illustrates a diagram of the distribution of the particles 700 at time t=0 seconds. FIG. 7B depicts a diagram of the distribution of the particles 710 at time t=1.5 seconds. FIG. 7C illustrates a diagram of the distribution of the particles 720 at time t=3 seconds. FIG. 7D illustrates a diagram of the distribution of the particles 730, which can reach their steady-state by t=5 seconds and remain trapped thereafter. As shown in FIG. 7D, the trapped particles are formed into a well-defined diffraction grating.

With the particles being electronically manipulated and trapped, as desired, it can be desirable to detect the particles. Given the submicron size of the particles, the particles cannot be detected using conventional macro-scale optical detection systems or techniques. In accordance with an embodiment, the subject innovation can facilitate detecting small scale particles (e.g., submicron particles) using innovative macro-scale optical detection systems, devices, and methodologies.

Referring again to diffraction gratings, a diffraction grating is a reflecting or transparent element whose optical properties are periodically modulated. A diffraction grating is commonly realized as parallel and equally spaced grooves on a material surface. The simulations of the above-described simulation demonstrate how the systems, methodologies, and devices (e.g., electronic manipulation of particles using a lab-on-chip), such as disclosed herein, can be used to arrange particles (e.g., one or more disparate types of submicron particles) into a structure having this diffraction grating form.

Figure 8:
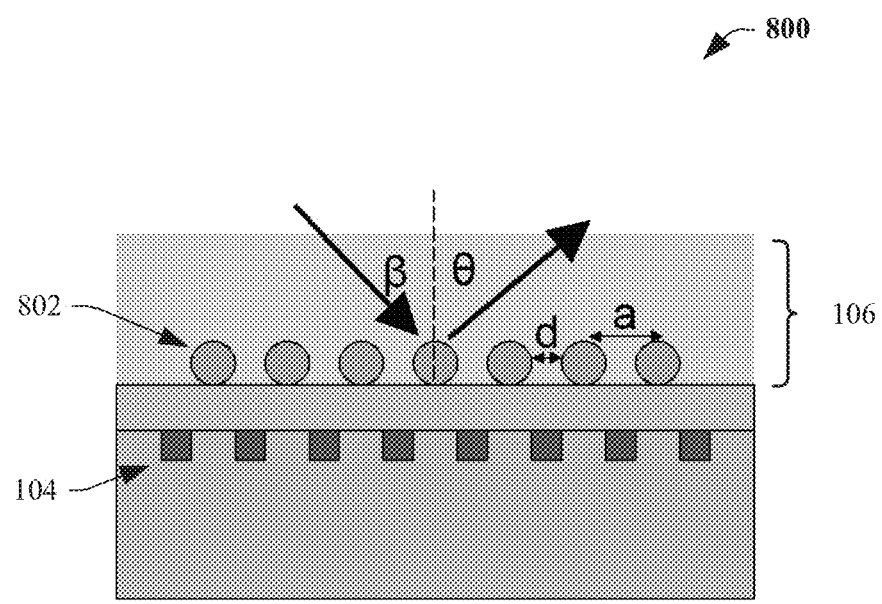
FIG. 8 depicts a cross section of an example portion of a cross section of a lab-on-chip with dielectrophoretically trapped particles arranged to form a diffraction grating in accordance with an aspect of the disclosed subject matter.

Referring to FIG. 8, depicted is a cross section of an example portion of a cross section of a particle manipulation device 800 (e.g., device 100, device 300, device 400) with dielectrophoretically trapped particles arranged to form a diffraction grating in accordance with an aspect of the disclosed subject matter. In one aspect, particles 802 can be trapped in a line formation in the gap spacing between adjacent electrodes 104 (e.g., as in FIG. 7D) using dielectrophoresis. For a groove spacing d and a wavelength λ incident at angle β, the grating equation given by:

$$m\lambda = d(\sin\theta + \sin\beta) \quad (6)$$

can give the value of the diffraction angle θ at which constructive interference will occur in the m$^{th}$ diffractive order. If it is assumed that the particles 802 being trapped are opaque and the bottom surface of the fluidic chamber 106 of the particle manipulation device 800 is made to be reflective, the intensity of diffracted light as a function of its angle of observation angle is:

$$I(\theta) = I_0 \left[\operatorname{sinc}\left(\frac{\pi d}{\lambda}\sin\theta\right)\right]^2 \cdot \left[\frac{\sin\left(\frac{N\pi a}{\lambda}\sin\theta\right)}{\sin\left(\frac{\pi a}{\lambda}\sin\theta\right)}\right]^2 \quad (7)$$

where $I_0$ is the measured intensity for the single slit diffraction case, a is the center to center pitch of the trapped particles 802, and N is the number of grating slits that are illuminated.

Respective types of small scale particles (e.g., nanometer scale in size) can be detected and/or assayed based at least in part on information obtained from measurements of the optical power, the diffraction angle, and/or other information, when a light beam of a specified wavelength is transmitted onto the diffraction grating of particles, or a portion thereof. When a light beam of a specified wavelength is shown on the diffraction grating, an optical readout of optical power of diffracted light at an angle that corresponds to one of the diffraction orders (e.g., first order, second order, third order, ...) for the diffraction grating can be obtained from the light diffracted off the diffraction grating. The angle is determined by the wavelength of the incident light beam, the distance between adjacent grating lines (e.g., spatial period), and the diffraction order selected. The optical power of diffracted light at the detection angle can depend on the optical power at the readout wavelength of the incident light beam, the diffraction order selected, and the efficiency of the diffraction grating. The efficiency of the diffraction grating is related to density of particles trapped into the lines of the diffraction grating. Information related to the measured optical power of the diffracted light at the corresponding diffraction angle when diffracted from a region of the spatial grating pattern, which can be populated with particles of a specific type, can be compared to known particle assays to obtain accurate measurements of particle populations to facilitate detection and assay of the particles of interest in the buffer solution.

Figure 9:
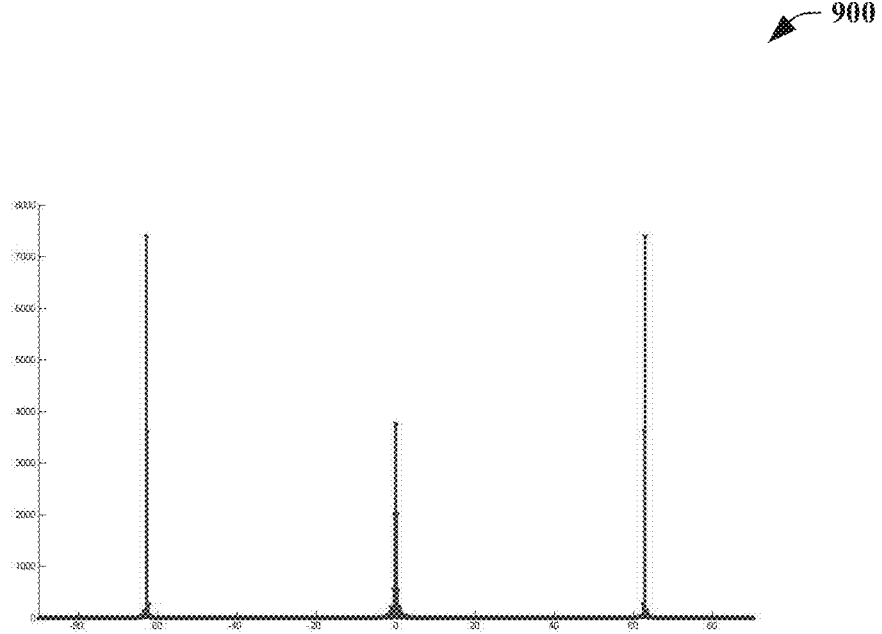
FIG. 9 illustrates an example graph of the distribution of optical power in diffracted light to specific angles corresponding to the $0^{th}$ and $1^{st}$ diffraction order when a 400 nm source illuminates 2,048 lines of particles that are 250 nm in diameter and are trapped at a pitch of 450 nm in accordance with an aspect of the disclosed subject matter.

FIG. 9 illustrates an example graph 900 of the distribution in diffracted light to specific angles corresponding to the 0$^{th}$ and 1$^{st}$ diffraction order when a 400 nm source illuminates 2,048 grooves of particles that are 250 nm in diameter and are trapped at a pitch of 450 nm in accordance with an aspect of the disclosed subject matter. The creation of this diffraction pattern, as illustrated in graph 900, allows the presence of particles to be sensed (e.g., detected) using macro-scale optical detectors, alleviating the need for submicron detection techniques.

Figure 10:
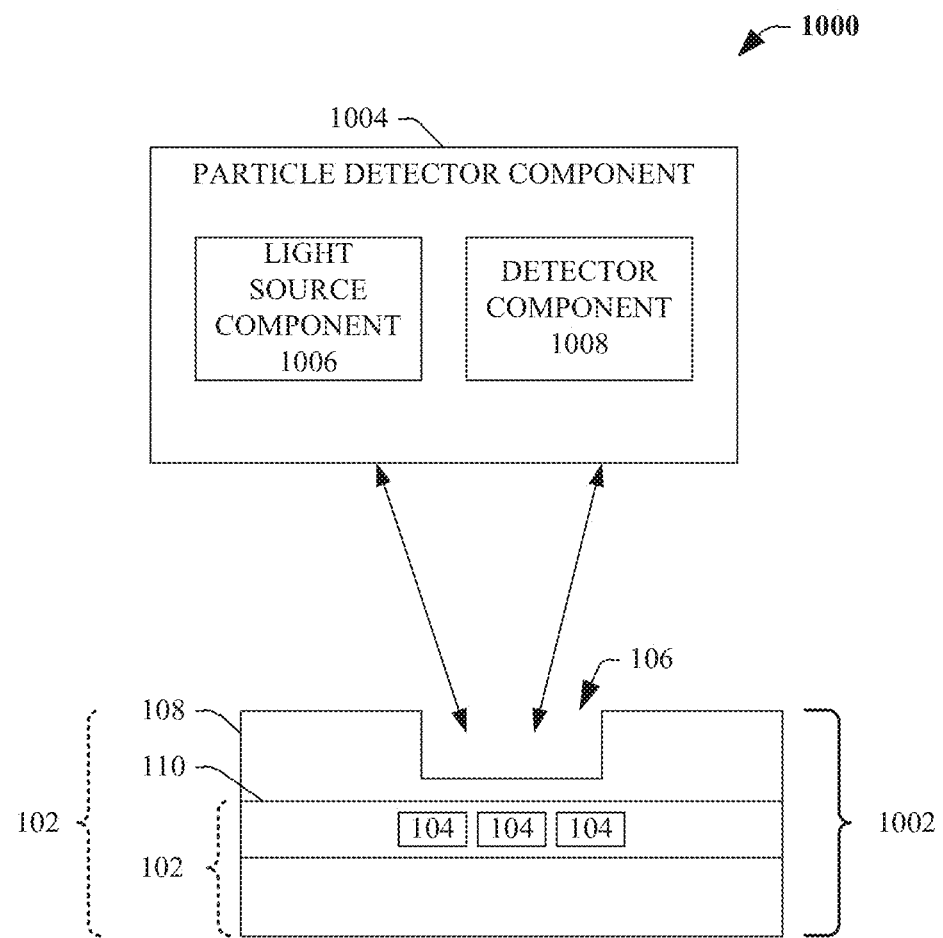
FIG. 10 depicts a block diagram of a system that can facilitate electronic manipulation and detection of small scale particles in accordance with an aspect of the disclosed subject matter.

Turning to FIG. 10, depicted is a block diagram of a system 1000 that can facilitate electronic manipulation and detection of small scale particles in accordance with an aspect of the disclosed subject matter. System 1000 can include a lab component 1002 that can facilitate electronically manipulating particles of interest (e.g., submicron particles) to trap and arrange the particles, as desired (e.g., trap and arrange the particles in a diffraction grating). The lab component 1002 (e.g., lab-on-chip) can comprise a IC chip 102 that can contain a plurality of electrodes 104 formed in an active semiconductor layer(s) 110 of the IC chip 102, a fluidic containment structure 108 with one or more fluidic chambers 106 formed therein. The IC chip 102, plurality of electrodes 104, fluidic chamber(s) 106, fluid containment structure 108, each can be the same or similar as, and/or can comprise the same or similar structure and/or functionality as, respective components such as more fully described herein, for example, with regard to device 100, device 300, and device 400.

In accordance with various embodiments, the lab component 1002 also can comprise digital and/or analog electronic components (e.g., control components 304, selector components 308) (not shown) that can facilitate controlling and selecting desired voltage waveforms that can be applied to the electrodes. In one embodiment, the digital and/or analog electronic components can be on the IC chip 102. In another embodiment, the digital and/or analog electronic components can be on one or more disparate IC chips (e.g., first IC chip 302, second IC chip 306), which can be positioned in a vertically tiered manner along with IC chip 102, for example.

In accordance with an aspect, the lab component 1002 can be structured so that the plurality of electrodes 104 can be formed on the active semiconductor layer(s) 110 of the IC chip 102, so the electrodes can be structured with the smallest feature size (or at least a significantly smaller feature size) that can be supported by the IC chip 102, such that the electrodes 104, other components, and vias formed thereon can have the smallest (or significantly smaller) feature size (e.g., nanometer in scale with regard to electrode size and electrode-to-electrode spacing) as compared to components formed on other layers, such as the metal interconnection layers, of the IC chip 102. For instance, each of the plurality of electrodes 104 can be submicron scale (e.g., nanometer scale) in size (e.g., 180 nm width or smaller). In another aspect, the plurality of electrodes 104 can be formed in a desired pattern (e.g., linear array; two-dimensional array, etc.). In still another aspect, the gap spacing between adjacent electrodes 104 in the array can be on a submicron scale (e.g., 270 nm or smaller gap spacing) to facilitate electronic manipulation of particles.

The orientation of the IC chip 102 (e.g., turned upside down so that the active semiconductor layer(s) 110 can be closer to the fluidic chamber(s) 106, and the metal interconnection layers are face down) and removal of at least a portion of the handle silicon from the third IC chip 102 can facilitate placing the plurality of electrodes 104 closer to the surface of the IC chip 102 and fluidic chamber(s) 106 and/or can facilitate creating the fluid containment structure 108, which can be formed of the handle silicon, as desired, in accordance with an embodiment. The fluidic chamber(s) 106 formed in the fluid containment structure 108 can be positioned so that the plurality of electrodes 104 can be in close proximity to the fluidic chamber(s) 106 (e.g., the fluidic chamber(s) 106 can be formed over the plurality of electrodes 104). The plurality of electrodes 104 being in close proximity to the fluidic chamber(s) 106, the submicron scale of the electrodes 104 (e.g., 180 nm or smaller width), and the submicron scale of the gap spacing (e.g., 270 nm or smaller gap spacing) between adjacent electrodes 104 in the linear electrode array, can facilitate optimizing (e.g., maximizing) the electric field strength, which can facilitate electronic manipulation (e.g., DEP) and detection of submicron particles contained in the buffer solution in the fluidic chamber(s) 106.

In another aspect, particles of interest (e.g., submicron particles, such as certain virus particles) can be contained in a buffer solution, which can be placed in a fluidic chamber(s) 106 of the lab component 1002. The lab component 1002 can facilitate manipulating the particles (e.g., using EP, DEP, and/or MFDEP) so that the particles can be arranged and trapped in regions of the fluidic chamber(s) 106 that are over the gap spacing between adjacent electrodes 104 to form a desired spatial pattern (e.g., diffraction grating). In an aspect, the control components (e.g., 204), each of which can be connected to corresponding selector components (e.g., 208), can facilitate controlling the selection of voltage waveforms having respective frequencies that can be applied to the electrodes 104. Based at least in part on the voltage waveform(s) of respective frequencies applied to the respective electrodes 104, the respective subsets of electrodes 104 can generate a spatially nonuniform electric field(s) that can be utilized to apply a corresponding force on the particles to manipulate and trap the particles in a desired formation without having to come in direct contact with the particles. For instance, the particles can be trapped in such a manner so as to form a desired pattern, such as a diffraction grating, where respective grating lines each can comprise particles of a specified type.

System 1000 also can comprise a particle detector component 1004 that can facilitate detecting particles (e.g., trapped particles) of a small scale size (e.g., submicron scale size) via innovative macro-scale optical detection. In an aspect, the particle detector component 1100 can comprise a light source component 1006 that can apply a light beam to particles that have been trapped to form a defined spatial pattern (e.g., linear pattern, two-dimensional pattern, regular pattern, irregular pattern). The particle detector component 1104 also can include a detector component 1108 that can detect interaction of the defined spatial pattern with the incident light beam to facilitate detection and assay of the trapped particles. In another aspect, to facilitate detection of the particles, the bottom surface of the fluidic chamber(s) 106 can be structured so that it is reflective (e.g., a reflective material can be formed, deposited, or coated on at least a portion of the surface of the fluidic chamber(s) 106).

For example, the light source component 1006 can apply a desired beam of light (e.g., having a desired wavelength that can be visible or subvisible) to a diffraction grating of particles of interest at a predefined angle β, where the diffraction pattern of the diffraction grating can facilitate sensing (e.g., detecting) the particles using the light beam applied thereto. The detector component 1008 can facilitate detecting and assaying particles contained in the diffraction grating based at least in part on characteristics of light reflected off the diffraction grating. For instance, when the light source component 1006 transmits a light beam having a specified wavelength to the diffraction grating, the detector component 1008 can determine the diffraction angle θ of the reflected light beam (e.g., diffracted light) at a selected diffraction order, as the light beam from the light source component 1006 reflects of the diffraction grating and particles contained therein. The diffraction angle can be determined by the wavelength of the incident light beam, the distance between adjacent grating lines (e.g., spatial period), and the diffraction order selected.

The detector component 1008 also can measure optical power of diffracted light at an angle that corresponds to the selected diffraction order for the diffraction grating, or portion thereof (e.g., $I(\theta)$ as described with regard to FIG. 8 and Equation 7). In an aspect, the detector component 1008 (e.g., one or more detectors) can be positioned at a desired angle(s) to facilitate measuring the optical power. The optical power of diffracted light at the detection angle can depend on the optical power at the readout wavelength of the incident light beam, the diffraction order selected, and the efficiency of the diffraction grating. Further, the measured optical power can correspond to the amount of interaction between the incident light beam and the diffraction grating, where the amount of interaction can correspond to the density of the particles in the diffraction grating. The measured optical power can be compared to known particle assays to obtain accurate measurements of particle populations in the buffer solution to facilitate detection and assay of the particles of interest in the buffer solution.

As another example, the light source component 1006 can apply an incident light beam to a defined spatial pattern comprising particles, where the defined spatial pattern can be an irregular or a nonuniform pattern. The interaction between the incident light beam and the defined spatial pattern can result in an image being formed, which can be detected by the detector component 1008. The image can be in the form of a hologram, for example. Thus, system 1000 can efficiently electronically manipulate particles to arrange particles in a desired manner, and can employ a particle detector component 1004 that can employ macro-scale optical detection of particles to facilitate detecting and assaying particles of interest in the buffer solution.

The aforementioned systems and devices have been described with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component providing aggregate functionality. The components may also interact with one or more other components not specifically described herein for the sake of brevity, but known by those of skill in the art.

FIGS. 11-14 illustrate methodologies and/or flow diagrams in accordance with the disclosed subject matter. For simplicity of explanation, the methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device, carrier, or media.

Figure 11:
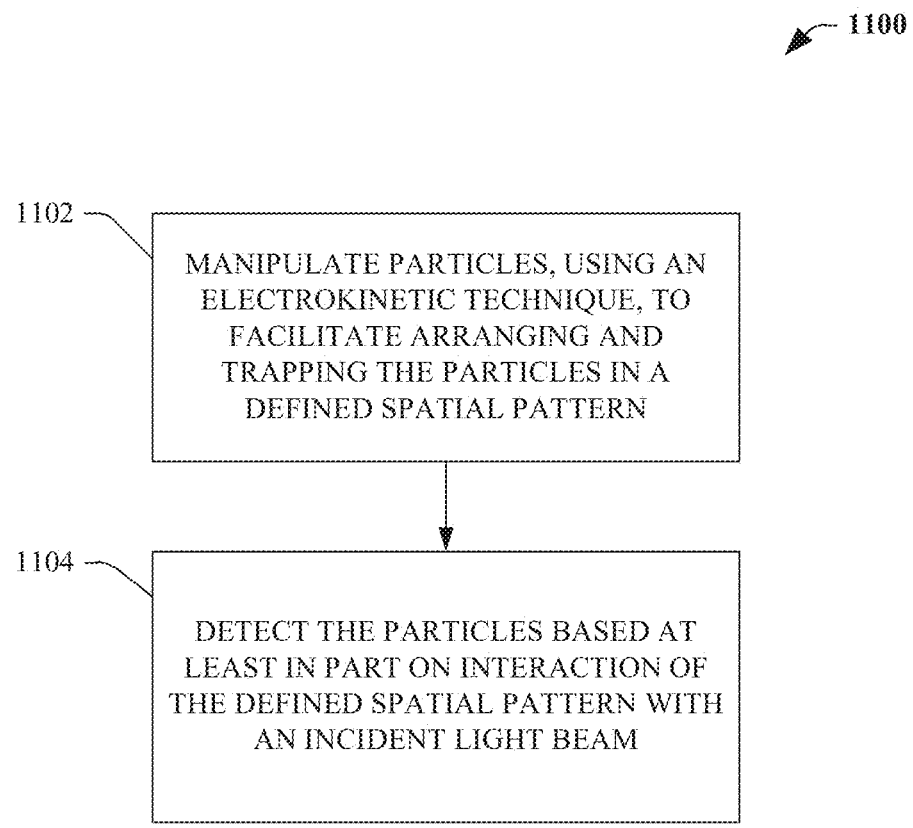
FIG. 11 illustrates a representative flow diagram of a methodology that can facilitate electronically manipulating and detecting small scale particles in accordance with an aspect of the disclosed subject matter.

Turning now to FIG. 11, depicted is a methodology 1100 that can facilitate electronic manipulation and detection of small scale particles (e.g., submicron scale particles) in accordance with an aspect of the disclosed subject matter. At 1102, particles can be manipulated, using an electrokinetic technique, to facilitate arranging and trapping the particles in a defined spatial pattern based at least in part on respective physical properties of respective particles (e.g., size, mass, electrical conductivity, . . . ) and at least one nonuniform electric field applied to the particles by a subset(s) of electrodes 104. The particles can be contained in a buffer solution in a fluidic chamber(s) 106 that can be in close proximity to a plurality of electrodes 104. In one aspect, the at least one nonuniform electric field can be generated as a function of at least one voltage waveform of a specified frequency(ies) applied to the subset(s) of electrodes, wherein the particles and the subset(s) of electrodes can be submicron in scale.

In one aspect, employing DEP, the particles can be manipulated to arrange, sort, and/or trap particles in a desired spatial pattern, such as a diffraction grating, based at least in part on respective physical properties of respective particles and one or more nonuniform electric fields that can be applied to the particles by a subset(s) of electrodes 104. The particles (e.g., submicron scale particles) can comprise a mixture of one or more disparate types of particles and each type of particle can be arranged in one or more grating lines in the diffraction grating. A subset(s) of electrodes 104 can receive a voltage waveform(s) having a desired frequency(ies), which can cause the subset(s) of electrodes 104 to provide a respective spatially nonuniform electric field(s) that can manipulate and trap the particles, or subset thereof, based at least in part on the respective physical properties of the particles.

At 1104, the particles can be detected based at least in part on interaction of the defined spatial pattern with an incident light beam. For instance, when the particles are arranged to form a diffraction grating, the particles can be detected based at least in part on the wavelength of a light beam applied to at least a portion of the diffraction grating and characteristics (e.g., diffraction angle, optical power) of light diffracted from the at least a portion of the diffraction grating. In accordance with an aspect, a light beam (e.g., visible or subvisible light) having a desired wavelength can be applied to at least a portion of the diffraction angle of particles (e.g., diffraction grating). The diffraction angle can be determined based in part on the wavelength of the applied light, the distance between adjacent grating lines of particles, and the diffraction order selected (e.g., as selected by a user). The optical power at the diffraction angle can be measured and can be dependent on optical power at the readout wavelength of the applied light, the diffraction order selected, and efficiency of the diffraction grating. The detected or measured characteristics of the light diffracted from the diffraction grating, or portion thereof, can be calibrated against known particle assays to obtain accurate measurements of particle populations in the diffraction grating, or portion thereof to facilitate detection and assay of particles of interest in the buffer solution. As a result, submicron scale particles can be detected and assayed employing innovative macro-scale optical detection. At this point, methodology 1100 can end.

Figure 12:
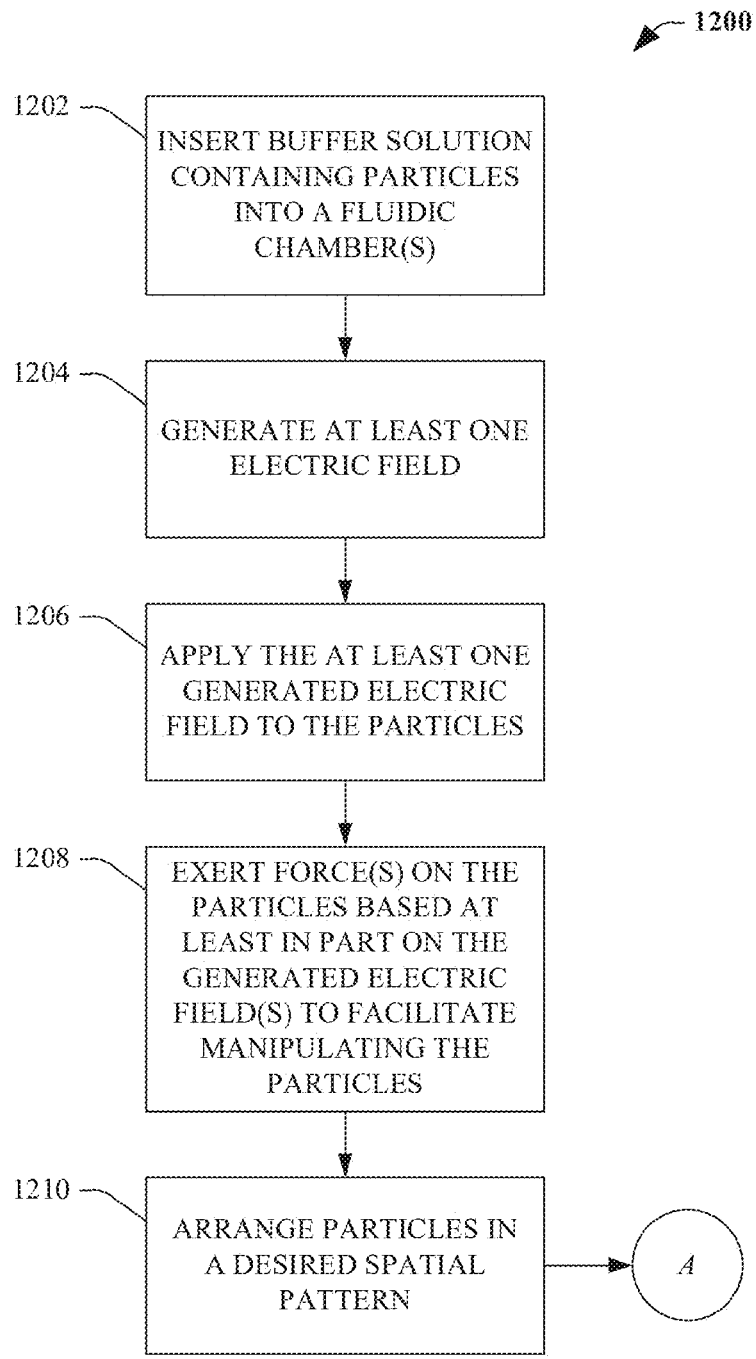
FIG. 12 illustrates a representative flow diagram of a methodology that can apply voltage waveforms at desired frequencies to facilitate electronically manipulating and detecting small scale particles in accordance with an aspect of the disclosed subject matter.

Turning to FIG. 12, illustrated is a methodology 1200 that can apply a desired number of voltage waveforms at desired frequencies to facilitate electronically manipulating and detecting small scale particles in accordance with an aspect of the disclosed subject matter. At 1202, a buffer solution that can contain particles of interest (e.g., one or more disparate types of submicron scale particles) can be inserted into a fluidic chamber(s) 106. In one aspect, a particle manipulation device (e.g., device 100, device 300, device 400), such as a lab-on-chip, can comprise one or more fluidic chambers 106 formed in a fluid containment structure 108 of the particle manipulation device.

In another aspect, the particle manipulation device can be formed so that electrodes 104, which can be contained on an active semiconductor layer(s) 110 of an IC chip 102, where the active semiconductor layer(s) 110 can be positioned directly under the fluid containment structure 108. The IC chip 102 can be oriented so that its handle silicon region can be face up and its metal interconnect layers can be face down. The IC chip 102 can have at least a portion of its handle silicon removed so that the active semiconductor layer(s) 110 can be exposed or at least closer to the face-up surface of the IC chip 102, so the electrodes 104 formed thereon can be placed in close proximity to the fluidic chamber(s) 106 in the fluid containment structure 108 to facilitate electronic manipulation (e.g., employing DEP) and detection of particles contained in the buffer solution. As the active semiconductor layer(s) 110 can support the smallest size components (or at least substantially smaller sized components) on the IC chip 102, the electrodes 104 can be formed so that they are submicron in size (e.g., width of 180 nm or smaller) and the gap spacing between adjacent electrodes 104, which can be formed in a linear electrode array, can be submicron in size (e.g., gap spacing can be 270 nm or smaller).

At 1204, at least one desired electric field (e.g., spatially nonuniform electric field(s)) can be generated. In one aspect, the particle manipulation device can generate one or more desired electric fields to facilitate manipulating (e.g., moving and arranging) the particles. The particle manipulation device can comprise a plurality of selector components (e.g., 308) that can be connected to corresponding electrodes 104 to facilitate providing a selected voltage waveform(s), where each waveform can have a respective desired frequency, to a subset(s) of electrodes 104 at each clock cycle. The selector components can be connected to corresponding control components (e.g., 304), which can facilitate controlling selection of the voltage waveforms on the rising edge of each clock cycle. The voltage waveforms can be external voltage waveforms and/or voltage waveforms generated by the particle manipulation device. The selected voltage waveforms can be provided to the subset(s) of electrodes 104 to facilitate generating the desired electric field(s) in order to facilitate manipulating the particles in the buffer solution in the fluidic chamber(s) 106.

In accordance with an aspect, more than one voltage waveform having a respective frequency can be applied to respective subset of electrodes 104 to facilitate manipulating the particles to sort and arrange different types of particles so particles of the same type can be grouped together in a region of a desired spatial pattern, for example, in one or more lines (e.g., parallel or substantially parallel lines) of a diffraction grating. The multiple voltage waveforms (having respective frequencies) can be applied sequentially or can be applied at the same time, as desired.

At 1206, the at least one generated electric field can be applied to the particles. In one aspect, the desired electric field(s) (e.g., spatially nonuniform electric field) generated by the electrodes 104 can be applied to the particles in the buffer solution. At 1208, a corresponding force(s) can be exerted on the particles based at least in part on the applied electric field(s). In one aspect, the electric field(s) applied to the particles in the buffer solution by the subset(s) of electrodes 104 can facilitate exerting a force(s) on the particles to facilitate manipulating the particles, based at least in part on the respective physical properties of the respective particles, to arrange and trap the particles in a desired spatial pattern in the fluidic chamber 106. At 1210, the particles can be arranged in a desired spatial pattern (e.g., diffraction grating). In an aspect, the electric force(s) applied by the subset(s) of electrodes 104 can facilitate manipulating the particles to arrange the particles in the fluidic chamber 106 so the particles can form the desired spatial pattern. The arranged particles can remain trapped in the desired spatial pattern. In one aspect, the particle manipulation device can trap the particles, which can be arranged in a desired spatial pattern, so that the particles can remain positioned in the form of a spatial pattern in the fluidic chamber(s) 106. At this point methodology can proceed to reference point A (e.g., where a methodology 1400 can be employed to facilitate detecting and assaying the manipulated particles). At this point, methodology 1200 can end.

Figure 13:
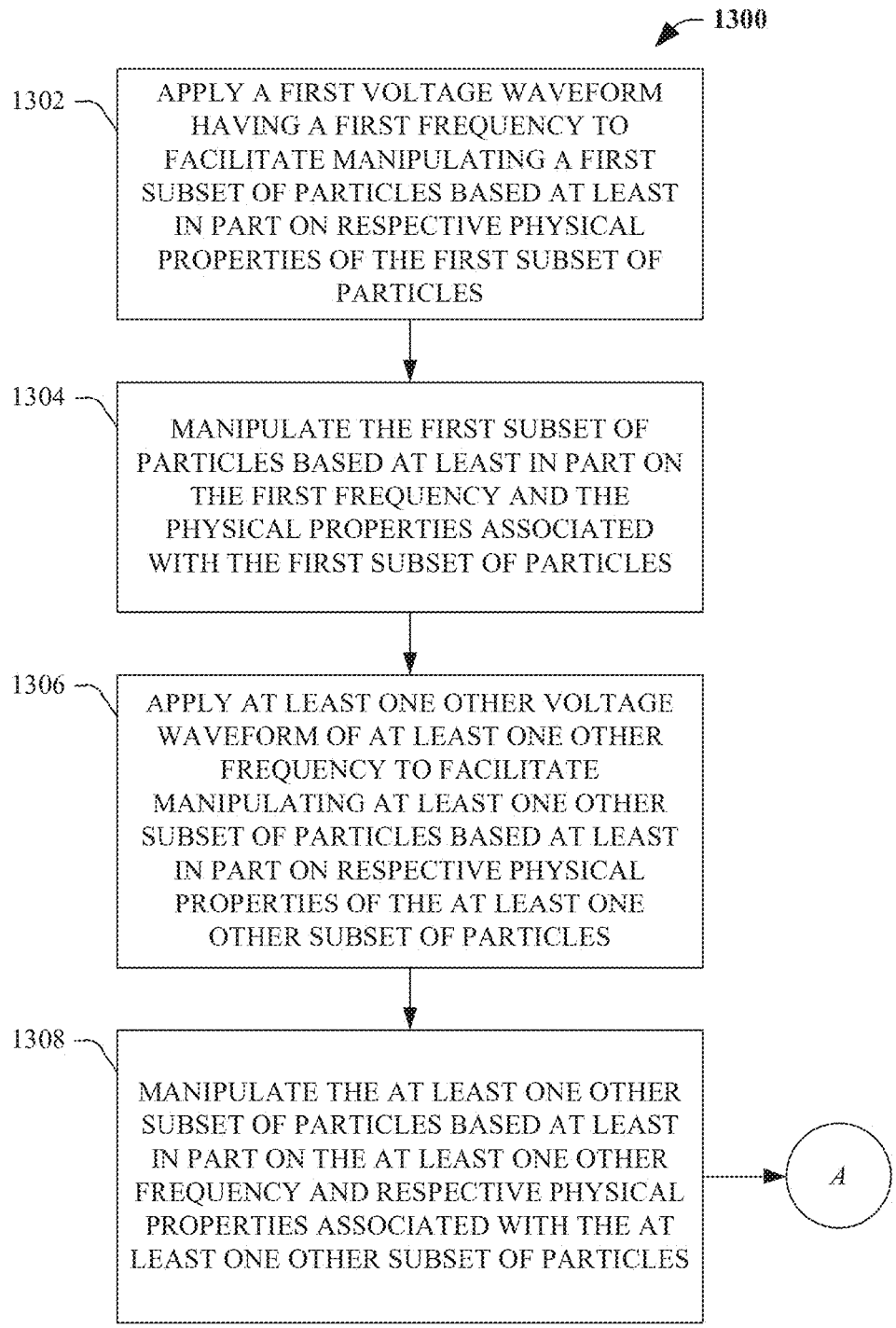
FIG. 13 depicts a representative flow diagram of a methodology that can facilitate electronically manipulating and detecting small scale particles via sequentially applying multiple frequencies in accordance with an aspect of the disclosed subject matter

FIG. 13 illustrates is a methodology 1300 that can facilitate electronically manipulating and detecting small scale particles via sequentially (e.g., in temporal sequences and/or spatial sequences) applying multiple frequencies (e.g., sequential MFDEP) in accordance with an aspect of the disclosed subject matter. A set of particles (e.g., one or more disparate types of particles) can be contained in a buffer solution placed in a fluidic chamber(s) 106 of a particle manipulation device (e.g., device 100, device 300, device 400), such as a lab-on-chip. At 1302, a first voltage waveform having a first frequency can be applied to facilitate manipulating a first subset of particles based at least in part on respective physical properties of the first subset of particles. In an aspect, the particles can be submicron scale in size (e.g., nanometer scale in size), and the electrodes 104 can be submicron scale in size with gap spacing between adjacent electrodes 104 that is submicron in size. The first voltage waveform can be applied to a first subset of electrodes 104 to facilitate generating a spatially nonuniform electric field that can be applied to the particles in the fluidic chamber 106 to facilitate manipulating (e.g., employing DEP) a first subset of particles (e.g., a portion or all of the particles in the set) in the fluidic chamber 106.

At 1304, the first subset of particles can be manipulated based at least in part on the first frequency and the physical properties (e.g., conductivity) associated with the first subset of particles. In an aspect, the first subset of particles can be moved and trapped in a region of the fluidic chamber 106 positioned over the first subset of electrodes 104. The first subset of particles can comprise a single type of particle or more than one type of particle, where each type of particle can comprise respective physical properties. For example, particles (e.g., one or more types of particles) having a conductivity, which is higher than a conductivity corresponding to the force applied to the particles based in part on the first frequency, can move in one direction in the fluidic chamber 106, and other particles (e.g., one or more types of particles) having a conductivity, which is lower than a conductivity corresponding to the force applied to the particles based in part on the first frequency, can move in another direction (e.g., opposite direction) in the fluidic chamber 106. The first subset of particles can be formed into one or more diffraction lines positioned along the gap spacing between adjacent electrodes 104 of the first subset of electrodes 104.

At 1306, at least one other voltage waveform of at least one other frequency can be applied to facilitate manipulating at least one other subset of particles based at least in part on respective physical properties of the at least one other subset of particles. In accordance with an embodiment, the at least one other voltage waveform of at least one other frequency can be applied sequentially (e.g., employing spatial and/or temporal sequences) to at least one other subset of electrodes 104. For instance, the particle manipulation device can apply a second voltage waveform of a second frequency to a second subset of electrodes 104 after the first voltage waveform has been applied to manipulate the first subset of particles. As desired, the particle manipulation device can apply one or more voltage waveforms having respective frequencies that can be applied to respective subsets of electrodes to facilitate progressively manipulating and separating (e.g., sorting) respective subsets of particles.

In an aspect, the particle manipulation device can select and apply the at least one other voltage waveform to at least one other subset of electrodes 104 to facilitate generating a spatially nonuniform electric field from the electrodes 104 that can be applied to the particles in the fluidic chamber 106 to facilitate manipulating the at least one other subset of particles. The at least one other subset of particles can be a subset of the particles in the first subset of particles or can be a subset of particles in another subset of particles depending in part on the frequency (e.g., the at least one other frequency) applied to the at least one other set of electrodes 104.

At 1308, the at least one other subset of particles can be manipulated, based at least in part on the at least one other frequency and respective physical properties (e.g., conductivity) associated with the at least one other subset of particles, to facilitate arranging particles into a defined spatial pattern. For example, the particle manipulation device can form the at least one other subset of particles into one or more diffraction lines positioned along the gap spacing between adjacent electrodes 104 of the at least one other subset of electrodes 104 to facilitate creating a diffraction grating wherein respective grating lines can contain a particular type of particle. At this point, methodology 1300 can proceed to reference point A (e.g., where a methodology 1400 can be employed to facilitate detecting and identifying the manipulated particles). At this point, methodology 1300 can end.

Figure 14:
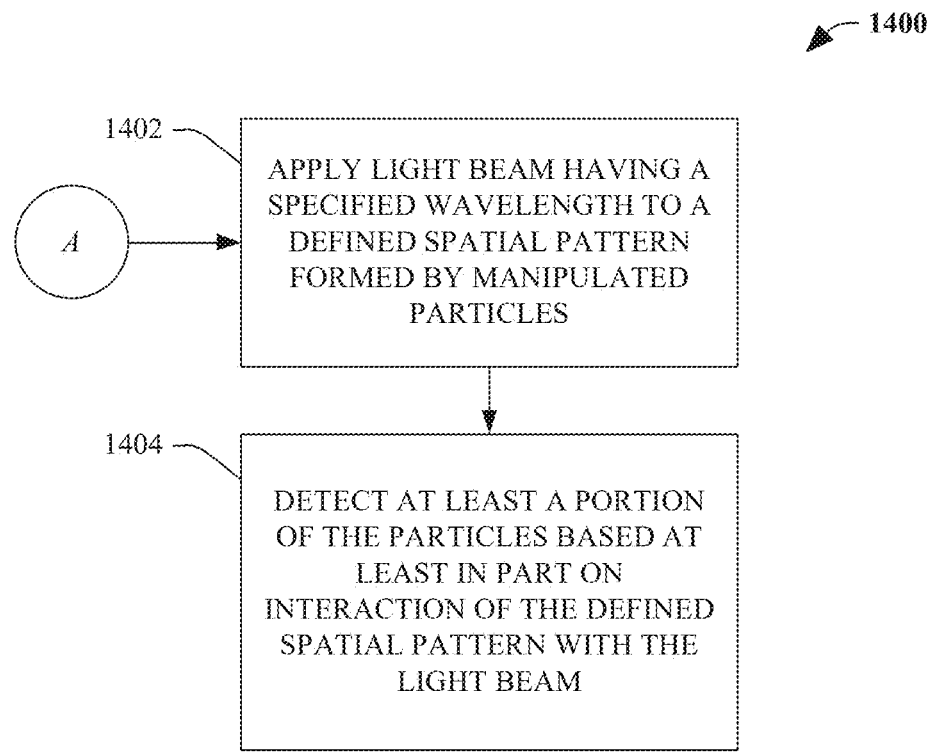
FIG. 14 depicts a representative flow diagram of a methodology that can facilitate detecting small scale particles in accordance with an aspect of the disclosed subject matter.

Turning to FIG. 14, depicted is a methodology 1400 that can facilitate detecting (e.g., optically detecting) small scale particles (e.g., submicron scale particles) in accordance with an aspect of the disclosed subject matter. In one aspect, particles can be arranged in the form of a defined spatial pattern (e.g., diffraction grating) in a fluidic chamber(s) 106 of a particle manipulation device (e.g., device 100, device 300, device 400), such as a lab-on-chip, for example, as described with regard to methodology 1200 or methodology 1300, where, by employing electronic manipulation techniques (e.g., DEP), at reference point A, the particles can be arranged trapped in the form of a defined spatial pattern. In accordance with another aspect, the fluidic chamber(s) 106, which can be formed in the fluid containment structure 108 of the particle manipulation device, can be formed or coated so that the surface (e.g., bottom surface) can be reflective to facilitate enhanced separation, isolation, and/or detection of particles.

At 1402, a light beam having a specified wavelength can be applied to a defined spatial pattern (e.g., diffraction grating) formed by manipulated particles. In accordance with an aspect, a particle detector component 1004 can facilitate applying a desired light beam (e.g., light beam with desired wavelength) at a desired angle to the defined spatial pattern, or portion thereof, formed by the trapped particles.

At 1404, at least a portion of the particles can be detected based at least in part on interaction of the defined spatial pattern with the light beam (e.g., incident light beam). For instance, when one or more types of particles are formed into a diffraction grating, all or at least a portion of the particles can be detected based at least in part on measured optical power of diffracted light at a corresponding diffraction angle $\theta$ when the light is diffracted from a region of the diffraction grating. When the light beam of specified wavelength is applied to a region of the diffraction grating, the particle detector component 1004 can facilitate measuring the optical power of diffracted light at the corresponding diffraction angle $\theta$ when the light is diffracted from the region of the diffraction grating. The magnitude of the optical power (e.g., $I(\theta)$) can be determined as a function of the diffraction angle of the light reflected off the region of the diffraction grating, where the diffraction angle corresponds to the selected diffraction order for the diffraction grating (e.g., as described herein with regard to FIG. 8 and Equation 7). The optical power at the detection angle (e.g., diffraction angle for the selected diffraction order) can depend on the optical power at the readout wavelength of the applied light beam, the diffraction order selected, and the efficiency of the diffraction grating. The diffraction angle can be determined as a function of the specified wavelength of the light beam, distance between adjacent lines of respective particles in the diffraction grating, and the diffraction angle of the light beam reflecting off the diffraction grating.

In an aspect, the measured optical power can correspond to the amount of interaction between the incident light beam and the diffraction grating, where the amount of interaction can correspond to density of particles in the diffraction grating. In another aspect, the measured optical power can be compared to known particle assays to obtain accurate measurements of particle populations in that region of the diffraction grating to facilitate detection and assay of the particles of interest in that region of the diffraction grating. For instance, the measured optical power associated with one particle type can different from the measured optical power associated with another particle type. In an aspect, the particle detector component 1004 can provide information, such as measured optical power, regarding the detected particles as an output, which can be perceived by a user and utilized to assay the particles. At this point, methodology 1400 can end.

It should be appreciated that the methodologies disclosed herein and throughout this specification are capable of being stored on an article of manufacture to facilitate transporting and transferring such methodologies to computers. The term article of manufacture, as used herein, is intended to encompass a computer program accessible from any computer-readable device, carrier, or media.

It should be appreciated that some portions of the detailed description have been presented in terms of algorithms and/or symbolic representations of operations on data bits that can be contained within a computer memory. These algorithmic descriptions and/or representations are the means employed by those cognizant in the art to most effectively convey the substance of their work to others equally skilled. An algorithm is here, generally, conceived to be a self-consistent sequence of acts leading to a desired result. The acts are those requiring physical manipulations of physical quantities. Typically, though not necessarily, these quantities take the form of electrical and/or magnetic signals capable of being stored, transferred, combined, compared, and/or otherwise manipulated.

As used in this application, the terms "component," "system," and the like can refer to a computer-related entity, either hardware, a combination of hardware and software, software, software in execution, and/or firmware. For example, a component may be, but is not limited to being, a process running on a processor, a processor, an object, an instance, an executable, a thread of execution, a program and/or a computer. By way of illustration, both an application running on a computer and the computer can be a component. One or more components may reside within a process and/or thread of execution and a component may be localized on one computer and/or distributed between two or more computers.

The word "exemplary" is used herein to mean serving as an example, instance, or illustration. Any aspect or design described herein as "exemplary" is not necessarily to be construed as preferred or advantageous over the other aspects or designs.

Furthermore, all or portions of the subject innovation may be implemented as a method, apparatus, or article of manufacture using standard programming and/or engineering techniques to produce software, firmware, hardware, or any combination thereof to control a computer to implement the disclosed innovation. The term "article of manufacture" as used herein is intended to encompass a computer program accessible from any computer-readable device, carrier, or media. For example, computer readable media can include but is not limited to magnetic storage devices (e.g., hard disk, floppy disk, magnetic strips . . . ), optical disks (e.g., compact disk (CD), digital versatile disk (DVD . . . )), smart cards, and flash memory devices (e.g., card, stick, key drive . . . ). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the disclosed subject matter.

What has been described above includes examples of aspects of the claimed subject matter. It is, of course, not possible to describe every conceivable combination of components or methodologies for purposes of describing the claimed subject matter, but one of ordinary skill in the art may recognize that many further combinations and permutations of the disclosed subject matter are possible. Accordingly, the disclosed subject matter is intended to embrace all such alterations, modifications and variations that fall within the spirit and scope of the appended claims. Furthermore, to the extent that the terms "includes," "has," or "having," or variations thereof, are used in either the detailed description or the claims, such terms are intended to be inclusive in a manner similar to the term "comprising" as "comprising" is interpreted when employed as a transitional word in a claim.

What is claimed is:

1. A device that facilitates detection of particles, comprising:
   a particle manipulation component that employs at least one electrokinetic technique to arrange a plurality of particles into a defined spatial pattern;
   a particle detector component that generates a light beam that is applied to at least a portion of the defined spatial pattern, wherein the defined spatial pattern interacts with the light beam such that the interaction is detectable to facilitate detection of the plurality of particles;
   at least one fluidic trench that contains the plurality of particles in a buffer solution; and
   a plurality of electrodes formed on an active silicon layer of an integrated circuit chip, wherein the integrated circuit chip is oriented so that a substrate of the integrated circuit chip is face up and a metal layer is face down, and wherein at least a portion of the substrate is removed to place the plurality of electrodes in close proximity to the at least one fluidic trench, which is positioned over the plurality of electrodes.

2. The device of claim 1, wherein the defined spatial pattern is a series of parallel lines that corresponds to a diffraction grating.

3. The device of claim 2, the particle detector component further comprises:
   at least one detector positioned at at least one angle and measures optical power at at least one angle corresponding to a diffraction order.

4. The device of claim 3, wherein the measured optical power corresponds to amount of interaction between the light beam and the diffraction grating, and the amount of interaction corresponds to density of particles in the diffraction grating.

5. The device of claim 4, information related to the measured optical power is compared to known particle assays to facilitate detection and assay of respective particles.

6. The device of claim 1, wherein the defined spatial pattern corresponds to a defined spatial pattern, wherein the defined spatial pattern interacts with the light beam to facilitate formation of an image.

7. The device of claim 6, wherein the image comprising a hologram.

8. The device of claim 6, wherein at least one detector detects the image.

9. The device of claim 1, wherein the at least one electrokinetic technique comprising is at least one of electrophoresis (EP), dielectrophoresis (DEP), or multiple frequency dielectrophoresis (MFDEP).

10. The device of claim 1, wherein at least a first subset of electrodes employs the at least one electrokinetic technique to facilitate manipulating the plurality of particles to form the defined spatial pattern based at least in part on at least one physical property of the particles and at least one voltage waveform of a specified frequency applied to the first subset of electrodes.

11. The device of claim 10, wherein at least one other subset of electrodes employs the at least one electrokinetic technique to facilitate manipulation of at least one subset of the plurality of particles to modify the defined spatial pattern so that disparate types of particles are separately grouped by particle type based at least in part on at least one respective physical property of the particles and respective voltage waveforms having respective frequencies applied to respective subsets of electrodes.

12. The device of claim 1, wherein a surface of the at least one fluidic trench is modified to enhance reflectivity of the surface to facilitate detection of the particles.

13. The method of claim 12, detecting the plurality of particles, further comprising:
   measuring optical power of the diffracted light at the corresponding diffraction angle of a specified diffraction order when light is diffracted from at least one region of the diffraction grating; and
   calibrating information related to the measured optical power against known particle assays to facilitate detection and assay of the respective particles.

14. The device of claim 13, wherein the measured optical power corresponds to amount of interaction between the incident light beam and the diffraction grating, and the amount of interaction corresponds to density of particles in the diffraction grating.

15. The method of claim 14, the measured optical power associated with the subset of particles of the first type is different from the measured optical power associated with the at least one other subset of particles of the at least one other type.

16. A method that facilitates manipulating and detecting particles, comprising:
   arranging a plurality of particles into a defined spatial pattern using at least one electrokinetic technique; and
   detecting the plurality of particles based at least in part on interaction of the defined spatial pattern with an incident light beam,
   wherein the defined spatial pattern is a diffraction grating comprising at least one diffraction grating line that contains a subset of particles of a first type and at least one other diffraction grating line that contains at least one other subset of particles of at least one other type.

* * * * *